US010493441B2

(12) United States Patent
Dinca et al.

(10) Patent No.: US 10,493,441 B2
(45) Date of Patent: Dec. 3, 2019

(54) COMPOSITIONS AND METHODS FOR SELECTIVE OLEFIN OLIGOMERIZATION COMPRISING METAL ORGANIC FRAMEWORKS

(71) Applicant: Massachusetts Institute of Technology, Cambridge, MA (US)

(72) Inventors: Mircea Dinca, Somerville, MA (US); Eric D. Metzger, Boston, MA (US); Carl K. Brozek, Seattle, WA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/760,104

(22) PCT Filed: Sep. 14, 2016

(86) PCT No.: PCT/US2016/051646
§ 371 (c)(1),
(2) Date: Mar. 14, 2018

(87) PCT Pub. No.: WO2017/048787
PCT Pub. Date: Mar. 23, 2017

(65) Prior Publication Data
US 2018/0250664 A1    Sep. 6, 2018

Related U.S. Application Data

(60) Provisional application No. 62/306,028, filed on Mar. 9, 2016, provisional application No. 62/218,003, filed on Sep. 14, 2015.

(51) Int. Cl.
*B01J 31/16* (2006.01)
*B01J 31/06* (2006.01)
(Continued)

(52) U.S. Cl.
CPC ........... *B01J 31/1691* (2013.01); *B01J 31/06* (2013.01); *B01J 31/16* (2013.01); *B01J 31/183* (2013.01);
(Continued)

(58) Field of Classification Search
None
See application file for complete search history.

(56) References Cited

U.S. PATENT DOCUMENTS 5,112,974 A    5/1992  Barton
6,893,564 B2   5/2005  Mueller et al.
(Continued)

FOREIGN PATENT DOCUMENTS

CN          104001476 B        5/2016
WO    WO 2014/182648 A1       11/2014
(Continued)

OTHER PUBLICATIONS

Canivet et al., "MOF-Supported Selective Ethylene Dimerization Single-Site Catalysts through One-Pot Postsynthetic Modification", J. Am. Chem. Soc. 2013, 135, 4195-4198. (Year: 2013).*
(Continued)

*Primary Examiner* — In Suk C Bullock
*Assistant Examiner* — Ali Z Fadhel
(74) *Attorney, Agent, or Firm* — Wolf, Greenfield & Sacks, P.C.

(57) ABSTRACT

Compositions and methods for selective olefin (e.g., ethylene) oligomerization comprising metal organic frameworks (MOFs) are generally provided In some embodiments, a MOF comprises a plurality of metal ions, each coordinated with at least one ligand comprising at least two unsaturated N-heterocyclic aromatic groups arranged about an organic core.

27 Claims, 13 Drawing Sheets

(51) Int. Cl.
      *C07C 2/32*      (2006.01)
      *B01J 31/18*     (2006.01)
(52) U.S. Cl.
      CPC ............ *B01J 31/1815* (2013.01); *C07C 2/32*
            (2013.01); *B01J 2231/20* (2013.01); *B01J*
            *2531/0205* (2013.01); *B01J 2531/0216*
            (2013.01); *B01J 2531/26* (2013.01); *B01J*
            *2531/847* (2013.01); *C07C 2531/22* (2013.01)

(56) References Cited

U.S. PATENT DOCUMENTS

| | | | |
|---|---|---|---|
| 7,215,473 | B2 | 5/2007 | Fleming |
| 7,662,746 | B2 | 2/2010 | Yaghi et al. |
| 8,197,579 | B2 | 6/2012 | Miller |
| 8,372,779 | B2 | 2/2013 | Schubert et al. |
| 8,764,887 | B2 | 7/2014 | Dinca et al. |
| 9,758,532 | B2 | 9/2017 | Dinca et al. |
| 2001/0003950 | A1 | 6/2001 | Zhang et al. |
| 2007/0171107 | A1 | 7/2007 | Wang |
| 2008/0188677 | A1 | 8/2008 | Schubert et al. |
| 2008/0306315 | A1 | 12/2008 | Lillerud et al. |
| 2009/0221418 | A1 | 9/2009 | Fischer et al. |
| 2010/0197990 | A1 | 8/2010 | Schubert et al. |
| 2010/0322837 | A1 | 12/2010 | Miller |
| 2011/0137100 | A1 | 6/2011 | Toulhoat et al. |
| 2011/0294658 | A1 | 12/2011 | Lefevre et al. |
| 2012/0077667 | A1 | 3/2012 | Liu et al. |
| 2012/0141685 | A1 | 6/2012 | Gaab et al. |
| 2013/0066128 | A1 | 3/2013 | Breuil et al. |
| 2013/0152789 | A1 | 6/2013 | Polshettiwar et al. |
| 2013/0204025 | A1 | 8/2013 | Buso et al. |
| 2014/0012039 | A1 | 1/2014 | Yaghi et al. |
| 2014/0326007 | A1* | 11/2014 | Dinca .................. C07F 3/06 62/112 |
| 2015/0047505 | A1 | 2/2015 | Schroder et al. |
| 2016/0102040 | A1 | 4/2016 | Allen et al. |
| 2017/0073364 | A1 | 3/2017 | Dinca et al. |
| 2017/0341010 | A1 | 11/2017 | Dinca et al. |

FOREIGN PATENT DOCUMENTS

| | | |
|---|---|---|
| WO | WO 2015/142954 A1 | 9/2015 |
| WO | WO 2015/171791 A1 | 11/2015 |
| WO | WO 2017/048795 A1 | 3/2017 |
| WO | WO 2018/067636 A1 | 4/2018 |

OTHER PUBLICATIONS

International Search Report and Written Opinion for PCT/US2016/051646 dated Dec. 2, 2016.
International Preliminary Report on Patentability for PCT/US2016/051646 dated Mar. 29, 2018.
Abbenhuis, Heterogenization of Metallocene Catalysts for Alkene Polymerization. Angew. Chem. Int. Ed. 1999;38(8):1058-60.
Achmann et al., Metal-Organic Frameworks for Sensing Applications in the Gas Phase. Sensors. 2009;9(3):1574-89. Epub Mar. 6, 2009.
Akiyama et al., Effect of functional groups in MIL-101 on water sorption behavior. Microporous and Mesoporous Materials. 2012;157:89-93.
Alarco-Padilla et al., Application of absorption heat pumps to multi-effect distillation: a case study of solar desalination. Desalination. Jun. 25, 2007;212:294-302.
Al-Sa'Doun, Dimerization of ethylene to butene-1 catalyzed by Ti(OR')4-AlR3. Applied Catalysis A. Nov. 2, 1993;105(1):1-40.
Askalany et al., An overview on adsorption pairs for cooling. Renewable and Sustainable Energy Reviews. Mar. 2013;19:565-72.
Baier et al., Post-Metallocenes in the Industrial Production of Polyolefins. Ange. Chemie Int. Ed. Sep. 8, 2014;53(37):9722-44.
Bellarosa et al. When the Solvent Locks the Cage: Theoretical Insight into the Transmetalation of MOF-5 Lattices and Its Kinetic Limitations. Chem. Mater. 2015;27(9):3422-9. Epub Apr. 13, 2015.
Bertrand et al., Thiophene-based covalent organic frameworks. PNAS. Mar. 26, 2013;110(13):4923-8. Epub Mar. 11, 2013.
Biswas et al., A cubic coordination framework constructed from benzobistriazolate ligands and zinc ions having selective gas sorption properties. Dalton Trans. 2009:6487-95. Epub Jun. 29, 2009.
Biswas et al., Homo- and Heteropentanuclear Coordination Compounds with Td Symmetry—the Solid State Structures of [MZn4(L)4(L')6] (M = CoII or Zn; L = chloride or acac; L' = 1,2,3-benzotriazolate). Z. Anorg. Allg. Chem. Oct. 2008;634(14):2532-8.
Biswas et al., Syntheses and Magnetostructural Investigations on Kuratowski-Type Homo- and Heteropentanuclear Coordination Compounds [MZn4C14(L)6] (MII = Zn, Fe, Co, Ni, or Cu; L = 5,6-Dimethyl-1,2,3-benzotriazolate) Represented by the Nonplanar $K_{3,3}$ Graph. Inorg. Chem. 2010;49(16):7424-34. Epub Jul. 16, 2010.
Bonaccorsi et al., Hydrothermal and microwave synthesis of SAPO (CHA) zeolites on aluminum foams for heat pumping applications. Microporous and Mesoporous Mater. 2013;167:30-37.
Boudjouk et al., Solvated and Unsolvated Anhydrous Metal Chlorides from Metal Chloride Hydrates. Inorg. Synth. 1992;29:108-11.
Brozek et al., Cation exchange at the secondary building units of metal-organic frameworks. Chem. Soc. Rev. 2014;43:5456-67. Epub May 16, 2014.
Brozek et al., Dynamic DMF Binding in MOF-5 Enables the Formation of Metastable Cobalt-Substituted MOF-5 Analogues. ACS Cent. Sci. 2015;1(5):252-60. Epub Jul. 29, 2015.
Brozek et al., Lattice-imposed geometry in metal-organic frameworks: lacunary Zn4O clusters in MOF-5 serve as tripodal chelating ligands for Ni2+. Chemical Science. 2012;3:2110-3. Epub Apr. 4, 2012.
Brozek et al., NO Disproportionation at a Mononuclear Site-Isolated Fe2+ Center in Fe2+-MOF-5. J. Am. Chem. Soc. 2015;137(23):7495-501. Epub May 19, 2015.
Brozek et al., Solvent-Dependent Cation Exchange in Metal-Organic Frameworks. Chem. Eur. J. Jun. 2, 2014;20(23):6871-4.
Brozek et al., Ti3+-, V2+/3+-, Cr2+/3+-, Mn2+-, and Fe2+-Substituted MOF-5 and Redox Reactivity in Cr- and Fe-MOF-5. J. Am. Chem. Soc. 2013;135(34):12886-91. Epub Jul. 31, 2013.
Cadiau et al., Design of Hydrophilic Metal Organic Framework Water Adsorbents for Heat Reallocation. Adv. Mater. 2015;27:4775-80. Epub Aug. 26, 2015.
Campbell et al., Chemiresistive Sensor Arrays from Conductive 2D Metal-Organic Frameworks. J. Am. Chem. Soc. 2015;137(43):13780-3. Epub Oct. 11, 2015.
Campbell et al., Cu3(hexaiminotriphenylene)2: An Electrically Conductive 2D Metal-Organic Framework for Chemiresistive Sensing. Angewandte Chemie Int Ed. Mar. 27, 2015;54(14):4349-52. Epub Feb. 9, 2015. Supporting Information Included.
Canivet et al., MOF-Supported Selective Ethylene Dimerization Single-Site Catalysts through One-Pot Postsynthetic Modification. J. Am. Chem. Soc. 2013;135:4195-8. Epub Mar. 7, 2013.
Canivet et al., Structure-property relationships of water adsorption in metal-organic frameworks. New J. Chem. 2014;38:3102-11. Epub Apr. 16, 2014.
Canivet et al., Water adsorption in MOFs: fundamentals and applications. Chem. Soc. Rev. 2014;43:5594-617. Epub May 29, 2014.
Caskey et al., Dramatic tuning of carbon dioxide uptake via metal substitution in a coordination polymer with cylindrical pores. J Am Chem Soc. Aug. 20, 2008;130(33):10870-1. doi: 10.1021/ja8036096. Epub Jul. 29, 2008.
Chen et al., Noncovalently Netted, Photoconductive Sheets with Extremely High Carrier Mobility and Conduction Anisotropy from Triphenylene-Fused Metal Trigon Conjugates. J Am Chem Soc. 2009;131(21):7287-92. Epub May 4, 2009.
Chmiola et al., Anomalous Increase in Carbon Capacitance at Pore Sizes Less Than 1 Nanometer. Science. Sep. 22, 2006;313(5794):1760-3.
Chmiola et al., Desolvation of Ions in Subnanometer Pores and Its Effect on Capacitance and Double Layer Theory. Angew. Chem. Int. Ed. Apr. 21, 2008;47(18):3392-5.

(56) References Cited

OTHER PUBLICATIONS

Choi et al., Broadly hysteretic H2 adsorption in the microporous metal-organic framework Co(1,4-benzenedipyrazolate). J Am Chem Soc. Jun. 25, 2008;130(25):7848-50. doi: 10.1021/ja8024092. Epub May 31, 2008.

Choi et al., Hydrogen storage in water-stable metal-organic frameworks incorporating 1,3- and 1,4-benzenedipyrazolate. Energy Environ. Sci. 2010;3:117-23. Epub Nov. 4, 2009.

Choi et al., Supported Single-Site Catalysts for Slurry and Gas-Phase Olefin Polymerisation. Can. J. of Chem. Eng. Jun. 2012;90:646-71.

Church et al., A New Multicomponent Reaction Catalyzed by a [Lewis Acid]+[Co(CO)4]-Catalyst: Stereospecific Synthesis of 1,3-Oxazinane-2,4-diones from Epoxides, Isocyanates, and Co. J. Am. Chem. Soc. 2007;129(26):8156-62. Epub Jun. 12, 2007. Abstract Only.

Church et al., Carbonylation of heterocycles by homogeneous catalysts. Chem. Commun. 2007;7:657-74. Epub Jan. 19, 2007.

Coasne et al., Temperature Effect on Adsorption/Desorption Isotherms for a Simple Fluid Confined within Various Nanopores. Adsorption. Jul. 2005;11:289-94.

Colombo et al., High thermal and chemical stability in pyrazolate-bridged metal-organic frameworks with exposed metal sites. Chem. Sci. 2011;2:1311-9. Epub Apr. 28, 2011.

Comito et al., Single-Site Heterogeneous Catalysts for Olefin Polymerization Enabled by Cation Exchange in a Metal-Organic Framework. J. Am. Chem. Soc. 2016;138(32):10232-7. Epub Jul. 21, 2016. Supporting Information Included.

Corma et al., Engineering Metal Organic Frameworks for Heterogeneous Catalysis. Chem. Rev. 2010;110(8):4606-55. Epub Apr. 1, 2010.

Critoph, Evaluation of alternative refrigerant—adsorbent pairs for refrigeration cycles. Applied Thermal Engineering. Nov. 1996;16(11):891-900.

Cui et al., An electroactive porous network from covalent metal-dithiolene links. Chem Commun. 2014;50:3986-8. Epub Feb. 24, 2014.

Cychosz et al., Water stability of microporous coordination polymers and the adsorption of pharmaceuticals from water. Langmuir. Nov. 16, 2010;26(22):17198-202. doi: 10.1021/la103234u. Epub Oct. 5, 2010.

De Lange et al., Adsorption-Driven Heat Pumps: The Potential of Metal—Organic Frameworks. Chem. Rev. 2015;115(22):12205-50. Epub Oct. 23, 2015.

De Lange et al., Metal—Organic Frameworks in Adsorption-Driven Heat Pumps: The Potential of Alcohols as Working Fluids. Langmuir. 2015;31(46):12783-96. Epub Nov. 2, 2015.

Denysenko et al., Elucidating Gating Effects for Hydrogen Sorption in MFU-4-Type Triazolate-Based Metal—Organic Frameworks Featuring Different Pore Sizes. Chem. Eur. J. 2011;17(6):1837-48. Epub Jan. 12, 2011.

Denysenko et al., Postsynthetic Metal and Ligand Exchange in MFU-41: A Screening Approach toward Functional Metal—Organic Frameworks Comprising Single-Site Active Centers. Chem. Eur. J. May 26, 2015;21(22):8188-99.

Denysenko et al., Reversible gas-phase redox processes catalyzed by Co-exchanged MFU-41(arge). Chem. Commun. 2012;48:1236-8. Epub Dec. 6, 2011.

Denysenko et al., Scorpionate-Type Coordination in MFU-41 Metal—Organic Frameworks: Small-Molecule Binding and Activation upon the Thermally Activated Formation of Open Metal Sites. Angew. Chemie Int. Ed. Jun. 2, 2014;53(23):5832-6.

Deria et al., Beyond post-synthesis modification: evolution of metal—organic frameworks via building block replacement. Chem. Soc. Rev. 2014;43:5896-912. Epub Apr. 11, 2014.

Desantis et al., Techno-economic Analysis of Metal—Organic Frameworks for Hydrogen and Natural Gas Storage. Energy Fuels. 2017;31(2):2024-32. Epub Jan. 4, 2017.

Dinca et al., Dalton Lecture: New Application of Metal-Organic Frameworks. UC Berkeley. Mar. 11, 2016. 49 pages.

Dinca et al., Designer Porous material for Clean Energy and Water. International Workshop on Advanced Materials. Al Hamra Fort, Ras al Khaimah, UAE. Feb. 2017. 7 pages.

Dinca et al., Teaching Sponges New Tricks: Redox Reactivity and Charge Transport in Microporous Metal-Organic Frameworks. Princeton University. Frick Chemistry Laboratory, Taylor Auditorium. Princeton, NJ. Sep. 14, 2015. 48 pages.

Dinca, Dynamic MOF SBUs as Active Sites for Small Molecule Reactivity and Catalysis. 253rd National ACS Meeting. San Francisco, CA. Apr. 2017. 10 pages.

Dinca, Teaching Sponges New Tricks: Small Molecule Chemistry and Charge Transport in Microporous Metal-Organic Frameworks. NSF Center for Chemical Innovation. Brown University. Providence, RI. May 2014. 4 pages.

Domski et al., Living alkene polymerization: New methods for the precision synthesis of polyolefins. Progress in Polymer Science. Jan. 2007;32(1):30-92.

Doonan et al., Exceptional ammonia uptake by a covalent organic framework. Nature Chemistry. 2010;2:235-8. Epub Feb. 7, 2010.

Ehrenmann et al., Water adsorption characteristics on MIL-101 for heat-transformation application of MOFs. Eur J Inorg Chem. 2011;2011(4):471-474.

Farrusseng et al., Metal—Organic Frameworks: Opportunities for Catalysis. Angew. Chemie Int. Ed. Sep. 28, 2009;48(41):7502-13.

Feigl et al., Über Verbindungen des Nickels mito-Phenylendiamin and 1, 3, 4-Toluylendiamin. Monatsh. Chem. Jul. 1927;48(7):445-50.

Férey et al., A Chromium Terephthalate-Based Solid with Unusually Large Pore Volumes and Surface Area. Science. Sep. 23, 2005;309(5743):2040-2.

Finiels et al., Nickel-based solid catalysts for ethylene oligomerization—a review. Catal. Sci. Technol. 2014;4:2412-26. Epub Apr. 16, 2014.

Froehlich et al., Multicycle water vapour stability of microporous breathing MOF aluminium isophthalate CAU-10-H. Dalton Trans. 2014;43:15300-4. Epub Aug. 26, 2014.

Furlan et al., Highly active zirconium(IV) catalyst containing sterically hindered hydridotris(pyrazolyl)borate ligand for the polymerization of ethylene. Macromolecular Rapid Communications. Oct. 2000;21(15):1054-7.

Furukawa et al., The chemistry and applications of metal-organic frameworks. Science. Aug. 30, 2013;341(6149):1230444. doi: 10.1126/science.1230444. 12 pages.

Furukawa et al., Water adsorption in porous metal-organic frameworks and related materials. J Am Chem Soc. Mar. 19, 2014;136(11):4369-81. doi: 10.1021/ja500330a. Epub Mar. 11, 2014.

Gandara et al., Porous, Conductive Metal-Triazolates and Their Structural Elucidation by the Charge-Flipping Method. Chem Eur J. Aug. 20, 2012;18(34):10595-601. Epub Jun. 22, 2012.

Garcia-Orozco et al., Tris(pyrazolyl)methane—chromium(III) complexes as highly active catalysts for ethylene polymerization. Journal of Molecular Catalysis A: Chemical. Dec. 2006;260(1-2):70-6.

Gargiulo et al., Synthesis and characterization of a microporous copper triazolate as a water vapor adsorbent. Microporous and Mesoporous Mater. 2011;145:74-9.

Garzón-Tovar et al., Optimised room temperature, water-based synthesis of CPO-27-M metal—organic frameworks with high space-time yields. J. Mater. Chem. A. 2015;3:20819-26. Epub Sep. 9, 2015.

Getzler et al., Synthesis of β-Lactones: A Highly Active and Selective Catalyst for Epoxide Carbonylation. J. Am. Chem. Soc. 2002;124(7):1174-5. Epub Jan. 24, 2002.

Gil et al., Copolymerization of Ethylene with 1-Hexene Using Sterically Hindered Tris(pyrazolyl)borate Titanium (IV) Compounds. Macromolecular Chemistry and Physics. Jan. 2001;202(2):319-24.

Golubovic et al., Sorption properties for different types of molecular sieve and their influence on optimum dehumidification performance of desiccant wheels. Int. J. Heat Mass Transf. Aug. 2006;49(17-18):2802-9.

Guo et al., Adsorption of NH3 onto activated carbon prepared from palm shells impregnated with H2SO4. Journal of Colloid and Interface Science. Jan. 15, 2005;281(2):285-90.

(56) References Cited

OTHER PUBLICATIONS

Gutzler et al., π-Electron Conjugation in Two Dimensions. J Am Chem Soc. 2013;135(44):16585-94. Epub Sep. 19, 2013.

Hao et al., Structurally Designed Synthesis of Mechanically Stable Poly(benzoxazine-co-resol)-Based Porous Carbon Monoliths and Their Application as High-Performance CO2 Capture Sorbents. J Am Chem Soc. 2011;133(29):11378-88. Epub Jun. 21, 2011.

Henninger et al., Characterisation and improvement of sorption materials with molecular modeling for the use of heat transformation applications. Adsorption. 2011;17:833-43.

Henninger et al., MOFs as adsorbents for low temperature heating and cooling applications. J Am Chem Soc. Mar. 4, 2009;131(8):2776-7. doi: 10.1021/ja808444z.

Henninger et al., MOFs for Use in Adsorption Heat Pump Processes. European Journal of Inorganic Chemistry. Jun. 2012; 2012(16):2625-34.

Henninger et al., Novel sorption materials for solar heating and cooling. Energy Procedia. 2012;30:279-88.

Henninger et al., Water adsorption characteristics of novel materials for heat transformation applications. Appl. Therm. Eng. 2010;30:1692-1702.

Herebian et al., Molecular and electronic structures of bis-(o-diiminobenzosemiquinonato)metal(II) complexes (Ni, Pd, Pt), their monocations and -anions, and of dimeric dications containing weak metal-metal bonds. J Am Chem Soc. Jul. 30, 2003;125(30):9116-28.

Hermes et al., Selective Nucleation and Growth of Metal-Organic Open Framework Thin Films on Patterned COOH/CF3-Terminated Self-Assembled Monolayers on Au(111). JACS. 2005;127:13744-5.

Hlatky, Heterogeneous Single-Site Catalysts for Olefin Polymerization. Chem. Rev. 2000;100:1347-76.

Hmadeh et al., New Porous Crystals of Extended Metal-Catecholates. Chemistry of Materials. 2012;24(18):3511-3. Epub Aug. 28, 2012.

House et al., The synthesis and X-ray structure of trans-[CrCl2(nPrNH2)4]BF4•H2O and the thermal and Hg2+-assisted chloride release kinetics from some trans-[CrCl2(N)4]+ complexes. Inorganica Chimica Acta. Sep. 1995;237(1-2):37-46.

Janchen et al., Studies of the water adsorption on Zeolites and modified mesoporous materials for seasonal storage of solar heat. Solar Energy. 2004;76:339-44.

Jasuja et al., Adjusting the Stability of Metal—Organic Frameworks under Humid Conditions by Ligand Functionalization. Langmuir. 2012;28(49):16874-80. Epub Nov. 7, 2012.

Jeon et al., Accelerated Life-time Tests including Different Load Cycling Protocols for High Temperature Polymer Electrolyte Membrane Fuel Cells. Electrochimica Acta. Dec. 1, 2014;148:15-25.

Jeremias et al., MIL-100(Al, Fe) as water adsorbents for heat transformation purposes—a promising application. J Mater Chem. 2012;22:10148-10151.

Jeremias et al., Programming MOFs for water sorption: amino-functionalized MIL-125 and UiO-66 for heat transformation and heat storage applications. Dalton Trans. Dec. 7, 2013;42(45):15967-73. doi: 10.1039/c3dt51471d. Epub Jul. 18, 2013.

Jeremias et al., Water and methanol adsorption on MOFs for cycling heat transformation processes. New J Chem. 2014;38:1846-52.

Kambe et al., Redox Control and High Conductivity of Nickel Bis(dithiolene) Complex π-Nanosheet: A Potential Organic Two-Dimensional Topological Insulator. J Am Chem Soc. 2014;136(41):14357-60. Epub Sep. 24, 2014.

Kambe et al., π-Conjugated Nickel Bis(dithiolene) Complex Nanosheet. J Am Chem Soc. 2013;135(7):2462-5. Epub Jan. 29, 2013.

Kaminsky et al., High melting polypropenes by silica-supported zirconocene catalysts. Makromol. Chem. Rapid. Commun. 1993;14:239-43.

Katz et al., High volumetric uptake of ammonia using Cu-MOF-74/Cu-CPO-27. Dalton Trans. 2016;45:4150-3. Epub Sep. 24, 2015.

Khutia et al., Water sorption cycle measurements on functionalized MIL-101 Cr for heat transformation application. Chem Mater. 2013;25:790-798.

Killian et al., Preparation of Linear α-Olefins Using Cationic Nickel(II) α-Diimine Catalysts. Organometallics. 1997;16(10):2005-7. Epub May 13, 1997.

Klet et al., Single-Site Organozirconium Catalyst Embedded in a Metal-Organic Framework. J. Am. Chem. Soc. 2015;137(50):15680-83. Epub Dec. 14, 2015.

Kobayashi et al., Conductivity, Doping, and Redox Chemistry of a Microporous Dithiolene-Based Metal—Organic Framework. Chem Mater. 2010;22(14):4120-2. Epub Jun. 25, 2010.

Kong et al., Opportunities in chemistry and materials science for topological insulators and their nanostructures. Nature Chemistry. 2011;3:845-9. Epub Oct. 24, 2011.

Kramer et al., Practical β-Lactone Synthesis: Epoxide Carbonylation at 1 atm. Org. Lett. 2006;8(17):3709-12. Epub Jul. 18, 2006.

Kreno et al., Metal-Organic Framework Materials as Chemical Sensors. Chemical Reviews. 2012;112(2):1105-25. Epub Nov. 9, 2011.

Kunrath et al., Highly Selective Nickel Ethylene Oligomerization Catalysts Based on Sterically Hindered Tris(pyrazolyl)borate Ligands. Organometallics. 2003;22:4739-43. Epub Oct. 9, 2003.

Kusgens et al., Characterization of metal-organic frameworks by water adsorption. Microporous and Mesoporous Mater. 2009;120:325-330.

Lallemand et al., Catalytic oligomerization of ethylene over Ni-containing dealuminated Y zeolites. Appl. Catal. A Gen. Feb. 2006;301:196-201.

Lallemand et al., Ethylene oligomerization over Ni-containing mesostructured catalysts with MCM-41, MCM-48 and SBA-15 topologies. Studies in Surface Science and Catalysis. 2007;170:1863-9. Epub Oct. 18, 2007.

Lallemand et al., Ni-MCM-36 and Ni-MCM-22 catalysts for the ethylene oligomerization. Studies in Surface Science and Catalysis. 2008;174:1139-42. Epub Nov. 6, 2008.

Li et al., Design and synthesis of an exceptionally stable and highly porous metal-organic framework. Nature. 1999;402:276-9. Epub Nov. 18, 1999.

Li et al., Highly active self-immobilized FI-Zr catalysts in a PCP framework for ethylene polymerization. Chem. Commun. 2015;51:16703-6. Epub Sep. 21, 2015.

Li et al., Reductive electrosynthesis of Crystalline Metal-Organic frameworks. JACS. 2011;133:12926-9.

Liao et al., Drastic Enhancement of Catalytic Activity via Post-oxidation of a Porous MnII Triazolate Framework. Chem. Eur. J. Sep. 1, 2014;20(36):11303-7.

Liu et al., High-Performance Chemical Sensing Using Schottky-Contacted Chemical Vapor Deposition Grown Monolayer MoS2 Transistors. ACS Nano. 2014;8(5):5304-14. Epub Apr. 21, 2014.

Liu et al., Postsynthetic modification of mixed-linker metal—organic frameworks for ethylene oligomerization. RSC Adv. 2014;4:62343-6. Epub Nov. 13, 2014.

Liu et al., Single-Walled Carbon Nanotube—Metalloporphyrin Chemiresistive Gas Sensor Arrays for Volatile Organic Compounds. Chem. Mater. 2015;27(10):3560-3. Epub May 8, 2015.

Low et al., Virtual high throughput screening confirmed experimentally: porous coordination polymer hydration. J. Am. Chem. Soc. Nov. 4, 2009;131(43):15834-42. doi: 10.1021/ja9061344.

Luna et al., Evaluation of Commercial Off-the-Shelf Sorbents and Catalysts for Control of Ammonia and Carbon Monoxide. American Institute of Aeronautics and Astronautics. 2008. 15 pages.

Ma et al., A series of isoreticular chiral metal—organic frameworks as a tunable platform for asymmetric catalysis. Nat. Chem. 2010;2:838-46. Epub Jul. 25, 2010.

Mahadevan et al., [Lewis Acid]+[Co(CO)4]—Complexes: A Versatile Class of Catalysts for Carbonylative Ring Expansion of Epoxides and Aziridines. Angew. Chem. Int. Ed. 2002;41(15):2781-4.

Makal et al., Methane storage in advanced porous materials. Chem Soc Rev. Dec. 7, 2012;41(23):7761-79. doi: 10.1039/c2cs35251f.

Maki et al., Electron Paramagnetic Resonance Studies of the Electronic Structures of Bis(maleonitriledithiolato) copper(II), -nickel(III), -cobalt(II), and -rhodium(II) Complexes. J. Am Chem. Soc. Nov. 1964;86(21):4580-7.

(56) References Cited

OTHER PUBLICATIONS

Marshall et al., Single-Crystal to Single-Crystal Mechanical Contraction of Metal-Organic Frameworks through Stereoselective Postsynthetic Bromination. J. Am. Chem. Soc. 2015;137:9527-30. Epub Jul. 15, 2015.
Merica et al., Synthesis of nitropolychlorinated dibenzo-p-dioxins (NPCDDs) and their photochemical reaction with nucleophiles. Can. J. Chem. 1995;73:826-35.
Metzger et al., Selective Dimerization of Ethylene to 1-Butene with a Porous Catalyst. ACS Cent. Sci. 2016;2(3):148-53. Epub Feb. 19, 2016. Supporting Information Included.
Miner et al., Electrochemical oxygen reduction catalysed by Ni3(hexaiminotriphenylene)2. Nat Commun. Mar. 2016;7:10942. 7 pages.
Mlinar et al., Selective Propene Oligomerization with Nickel(II)-Based Metal—Organic Frameworks. ACS Catal. 2014;4(3):717-21. Epub Jan. 27, 2014.
Mondloch et al., Destruction of chemical warfare agents using metal—organic frameworks. Nat. Mater. 2015;14:512-6. Epub Mar. 16, 2015.
Murtuza et al., Ethylene Polymerization Behavior of Tris(pyrazolyl)borate Titanium(IV) Complexes. Organometallics. 2002;21(9):1882-90. Epub Mar. 28, 2002.
Narayan et al., High Charge Mobility in a Tetrathiafulvalene-Based Microporous Metal—Organic Framework. J Am Chem Soc. 2012;134(31):12932-5. Epub Jul. 24, 2012.
Narayanan et al., Optimization of adsorption processes for climate control and thermal energy storage. Int. J. Heat Mass Transf. Oct. 2014;77:288-300.
Ng et al., Experimental investigation of the silica gel-water adsorption isotherm characteristics. Appl. Therm Eng. 2001;21:1631-42.
Nguyen et al., High Methanol Uptake Capacity in Two New Series of Metal—Organic Frameworks: Promising Materials for Adsorption-Driven Heat Pump Applications. Chem. Mater. 2016;28(17):6243-9. Epub Aug. 8, 2016.
Noro et al., Metal-organic thin-film transistor (MOTFT) based on a bis(o-diiminobenzosemiquinonate) nickel(II) complex. J Am Chem Soc. Jul. 20, 2005;127(28):10012-3.
Park et al., Cation-Dependent Intrinsic Electrical Conductivity in Isostructural Tetrathiafulvalene-Based Microporous Metal—Organic Frameworks. J. Am. Chem. Soc. 2015;137(5):1774-7. Epub Jan. 18, 2015.
Park et al., Heterogeneous Epoxide Carbonylation by Cooperative Ion-Pair Catalysis in Co(CO)4—Incorporated Cr-MIL-101. ACS Cent. Sci. 2017;3(5):444-8. Epbu Mar. 21, 2017. Supporting Information Included.
Park et al., Single-Ion Li+, Na+, and Mg2+ Solid Electrolytes Supported by a Mesoporous Anionic Cu—Azolate Metal—Organic Framework. J. Am. Chem. Soc. 2017;139(38):13260-3. Epbu Sep. 7, 2017.
Petit et al., The role of sulfur-containing groups in ammonia retention on activated carbons. Carbon. Mar. 2010;48(3):654-67.
Petit et al., Toward Understanding Reactive Adsorption of Ammonia on Cu-MOF/Graphite Oxide Nanocomposites. Langmuir. 2011;27(21):13043-51. Epub Oct. 4, 2011.
Pommier et al., Recent Advances in β-Lactone Chemistry. Synthesis. 1993;5:441-59.
Qajar et al., Enhanced ammonia adsorption on functionalized nanoporous carbons. Microporous and Mesoporous Materials. Dec. 2015 1;218:15-23.
Rieth et al., High and Reversible Ammonia Uptake in Mesoporous Azolate Metal—Organic Frameworks with Open Mn, Co, and Ni Sites. J. Am. Chem. Soc. 2016;138(30):9401-4. Epub Jul. 15, 2016. Supporting Information Included.
Rieth et al., Record Atmospheric Fresh Water Capture and Heat Transfer with a Material Operating at the Water Uptake Reversibility Limit. ACS Cent. Sci. 2017;3(6):668-72. Epub May 24, 2017. Supporting Information Included.
Ristic et al., The performance of small-pore microporous aluminophosphates in low-temperature solar energy storage: the structure-property relationship. Adv Func Mater. 2012;22:1952-7.
Saha et al., Fundamental and application aspects of adsorption cooling and desalination. Appl. Therm. Eng. Mar. 25, 2016;97:68-76.
Schmidt et al., A Readily Synthesized and Highly Active Epoxide Carbonylation Catalyst Based on a Chromium Porphyrin Framework: Expanding the Range of Available β-Lactones. Org. Lett. 2004;6(3):373-6. Epub Jan. 8, 2004.
Schmidt et al., Chromium(III) Octaethylporphyrinato Tetracarbonylcobaltate: A Highly Active, Selective, and Versatile Catalyst for Epoxide Carbonylation. J. Am. Chem. Soc. 2005;127(32):11426-35. Epub Jul. 16, 2005.
Schoenecker et al., Effect of water adsorption on retention of structure and surface area of metal-organic frameworks. Ind Eng Chem Res. 2012;51:6513-6519.
Severn et al., "Bound but Not Gagged"Immobilizing Single-Site α-Olefin Polymerization Catalysts. Chem. Rev. 2005;105:4073-147. Epub Oct. 22, 2005.
Shamir, New synthesis of chromium trichloride tetrahydrofuranate. Inorganica Chimica Acta. Feb. 15, 1989;156(2):163-4.
Sheberla et al., Conductive MOF electrodes for stable supercapacitors with high areal capacitance. Nature Materials. 2017;16:220-4. Epub Oct. 10, 2016. Supporting Information Included.
Sheberla et al., High Electrical Conductivity in Ni3(2,3,6,7,10,11-hexaiminotriphenylene)2, a Semiconducting Metal-Organic Graphene Analogue. J Am Chem Soc. 2014;136(25):8859-62. Epub Apr. 21, 2014. Supporting Information Included.
Shustova et al., Selective Turn-On Ammonia Sensing Enabled by High-Temperature Fluorescence in Metal-Organic Frameworks with Open Metal Sites. J Am Chem Soc. 2013;135(36):13326-9. Epub Aug. 27, 2013.
Speiser et al., Catalytic Ethylene Dimerization and Oligomerization: Recent Developments with Nickel Complexes Containing P,N-Chelating Ligands. Acc. Chem. Res. 2005;38(10):784-93. Epub Sep. 9, 2005.
Stavila et al., MOF-based electronic and opto-electronic devices. Chem Soc Rev. Aug. 21. 2014;43(16):5994-6010. doi: 10.1039/c4cs00096j.
Stiefel et al., The Myth of Nickel(III) and Nickel(IV) in Planar Complexes. J. Am. Chem. Soc. Jul. 1965;87(13):3016-7.
Stoeckli et al., Specific and non-specific interactions between ammonia and activated carbons. Carbon. 2004;42(8-9):1619-24.
Suh et al., Hydrogen storage in metal-organic frameworks. Chem Rev. 2012;112:782-835.
Sumida et al., Carbon dioxide capture in metal-organic frameworks. Chem Rev. Feb. 8, 2012;112(2):724-81. doi: 10.1021/cr2003272. Epub Dec. 28, 2011.
Sun et al., Electrically Conductive Porous Metal-Organic Frameworks. Angew Chem Int Ed Engl. Mar. 7, 2016;55(11):3566-79. doi: 10.1002/anie.201506219. Epub Jan. 8, 2016. Review.
Sun et al., Measuring and Reporting Electrical Conductivity in Metal-Organic Frameworks: Cd2(TTFTB) as a Case Study. J Am Chem Soc. 2016;138(44):14772-82. Epub Oct. 21, 2016.
Sun et al., Mn2(2,5-disulfhydrylbenzene-1,4-dicarboxylate): A Microporous Metal-Organic Framework with Infinite (-Mn-S-)∞ Chains and High Intrinsic Charge Mobility. J Am Chem Soc. 2013;135(22):8185-8. Epub May 14, 2013.
Svejda et al., Ethylene Oligomerization and Propylene Dimerization Using Cationic (α-Diimine)nickel(II) Catalysts. Organometallics. 1999;18(1):65-74. Epub Dec. 15, 1998.
Talin et al., Tunable electrical conductivity in metal-organic framework thin-film devices. Science. Jan. 3, 2014;343(6166):66-9. doi: 10.1126/science.1246738. Epub Dec. 5, 2013.
Tamainot-Telto et al., Carbon-ammonia pairs for adsorption refrigeration applications: ice making, air conditioning and heat pumping. International Journal of Refrigeration. Sep. 2009;32(6):1212-29.
Tatsidjodoung et al., A review of potential materials for thermal energy storage in building applications. Renew. Sust. Energ. Rev. 2013;18:327-49.
Teufel et al., MFU-4—A Metal-Organic Framework for Highly Effective H2/D2 Separation. Adv. Mater. Jan. 2013;25(4):635-9.

(56) References Cited

OTHER PUBLICATIONS

Theopold, Homogeneous Chromium Catalysts for Olefin Polymerization. Eur. J. Inorg. Chem. Jan. 1998;1:15-24.

Tonigold et al., Pyrazolate-based cobalt(II)-containing metal-organic frameworks in heterogeneous catalytic oxidation reactions: elucidating the role of entatic states for biomimetic oxidation processes. Chemistry. Jul. 25, 2011;17(31):8671-95. doi: 10.1002/chem.201003173. Epub Jun. 17, 2011.

Tulchinsky et al., Reversible Capture and Release of Cl2 and Br2 with a Redox-Active Metal—Organic Framework. J. Am. Chem. Soc. 2017;139(16):5992-7. Epub Mar. 28, 2017.

Van Humbeck et al., Ammonia Capture in Porous Organic Polymers Densely Functionalized with Brønsted Acid Groups. J. Am. Chem. Soc. 2014;136(6):2432-40. Epub Jan. 23, 2014.

Wade et al., Facile Deposition of Multicolored Electrochromic Metal—Organic Framework Thin Films. Angew Chem. Int. Ed. 2013;52(50):13377-81. Epub Oct. 16, 2013.

Wade et al., Investigation of the synthesis, activation, and isosteric heats of CO2 adsorption of the isostructural series of metal-organic frameworks M3(BTC)2 (M = Cr, Fe, Ni, Cu, Mo, Ru). Dalton Trans. Jul. 14, 2012;41(26):7931-8. doi: 10.1039/c2dt30372h. Epub Apr. 26, 2012.

Wade et al., Postsynthetic tuning of hydrophilicity in pyrazolate MOFs to modulate water adsorption properties. Energy Environ. Sci. 2013;6:2172-7.

Wade, Designing functionality for anion detection with molecular receptors and small molecule adsorption in microporous materials. PowerPoint Presentation. Brandeis University. Dec. 4, 2012. 50 pages.

Wang et al., A review on adsorption working pairs for refrigeration. Renewable and Sustainable Energy Reviews. Apr. 2009;13(3):518-34.

Wang et al., Organic topological insulators in organometallic lattices. Nat Commun. 2013;4:1471. Epub Feb. 12, 2012. 5 pages.

Wang et al., Prediction of a Two-Dimensional Organic Topological Insulator. Nano Lett. 2013;13(6):2842-5. Epub May 16, 2013.

Wang et al., Pyrazolate-Based Porphyrinic Metal—Organic Framework with Extraordinary Base-Resistance. J. Am. Chem. Soc. 2016;138(3):914-9. Epub Dec. 30, 2015.

Wickenheisser et al., Grafting of hydrophilic ethylene glycols or ethylenediamine on coordinatively unsaturated metal sites in MIL-100(Cr) for improved water adsorption characteristics. Inorganica Chimica Acta. 2013;407:145-52.

Wu et al., A Homochiral Porous Metal—Organic Framework for Highly Enantioselective Heterogeneous Asymmetric Catalysis. J. Am. Chem. Soc. 2005;127(25):8940-1. Epub Jun. 4, 2005.

Wu et al., Adsorption sites and binding nature of CO2 in prototypical metal-organic frameworks: a combined neutron diffraction and first-principles study. J Phys Chem Lett. 2010;1(13):1946-51.

Xiao et al., Oxidation of ethane to ethanol by N2O in a metal-organic framework with coordinatively unsaturated iron(II) sites. Nat Chem. Jul. 2014;6(7):590-5. doi: 10.1038/nchem.1956. Epub May 18, 2014.

Yamada et al., First-Principles Design of Half-Filled Flat Band of the Kagome Lattice in Two-Dimensinoal Metal-Organic Frameworks. Jul. 26, 2016. arXiv:1510.00164v3.

Yamazoe et al., Receptor Function and Response of Semiconductor Gas Sensor. Journal of Sensors. 2009;2009:21 pages.

Yang et al., Temperature-Triggered Collection and Release of Water from Fogs by a Sponge-Like Cotton Fabric. Adv. Mater. Feb. 25, 2013;25(8):1150-4.

Zhang et al., Ethylene Oligomerization Over Heterogeneous Catalysts. Energy and Environment Focus. Sep. 2014;3(3):246-56.

\* cited by examiner

COMPOSITIONS AND METHODS FOR SELECTIVE OLEFIN OLIGOMERIZATION COMPRISING METAL ORGANIC FRAMEWORKS

RELATED APPLICATIONS

This application is a national stage application under 35 U.S.C. § 371 of International Patent Application Serial No. PCT/US2016/051646, filed on Sep. 14, 2016, entitled "Compositions and Methods for Selective Olefin Oligomerization Comprising Metal Organic Frameworks," which claims priority to U.S. Provisional Patent Application Ser. No. 62/218,003, filed Sep. 14, 2015, and entitled "Compositions and Methods for Selective Olefin Oligomerization Comprising Metal Organic Frameworks" and U.S. Provisional Patent Application Ser. No. 62/306,028, filed Mar. 9, 2016, and entitled "Compositions and Methods for Selective Olefin Oligomerization Comprising Metal Organic Frameworks", each of which are incorporated herein by reference in their entirety for all purposes.

FIELD

Compositions and methods for selective olefin oligomerization comprising metal organic frameworks (MOFs) are generally provided. In some embodiments, a MOF comprises a plurality of metal ions, each metal ion coordinated with at least one ligand comprising at least two N-heterocyclic aromatic groups arranged about an organic core.

BACKGROUND

Ethylene is a cornerstone of the petrochemical industry. For example, the dimerization of ethylene to 1-butene plays a key role in the production of alkylate gasoline and of linear low-density polyethylene. Overall, ethylene oligomerization is one of the largest industrial transformations enabled by homogeneous catalysts, exceeded in volume only by hydroformylation, hydrocyanation, and methanol carbonylation. The prominence of ethylene dimerization in the overall industrial production of 1-butene is projected to rise further with the increasing reliance on natural gas feedstocks. Despite substantial academic and industrial efforts, the development of heterogeneous catalysts for ethylene dimerization has suffered from either a lack of activity or poor selectivity. Addressing the selectivity challenge is particularly difficult because, for example, small changes in the ligand sphere or electronic structure of the metal can change the relative rates of ethylene insertion versus beta-hydride elimination, which together relate to product distribution. Such degree of fine tuning in ligand design is the realm of homogeneous catalysis and has not traditionally been available to heterogeneous systems.

Accordingly, improved compositions and methods are needed.

SUMMARY

In some embodiments, a method for forming butene (e.g., 1-butene) from ethylene are provided, the method comprising exposing ethylene to a metal organic framework (MOF) catalyst to produce butene, wherein the MOF catalyst comprises a plurality of metal ions, each metal ion coordinated with at least one ligand, and wherein each ligand comprises at least two N-heterocyclic aromatic groups arranged about an organic core, wherein the N-heterocyclic aromatic groups are selected from the group consisting of imidazolate, triazolate, and tetrazolate.

In some embodiments, a method for forming butene (e.g., 1-butene) from ethylene is provided, the method comprising exposing ethylene to a metal organic framework (MOF) catalyst to produce butene, wherein the MOF comprises a plurality of metal ions, each metal ion coordinated with at least one ligand, and wherein butene is formed with a selectivity of at least about 95% and at a turnover frequency of at least about 20,000 per hour.

In some embodiments, the MOF comprising a plurality of metal ions (e.g., $Ni^{+2}$ and/or $Zn^{+2}$) and a plurality of ligands comprising one, two, three, or four N-heterocyclic aromatic groups (e.g., imidazolate, triazolate, and/or tetrazolate).

Figure 1A:
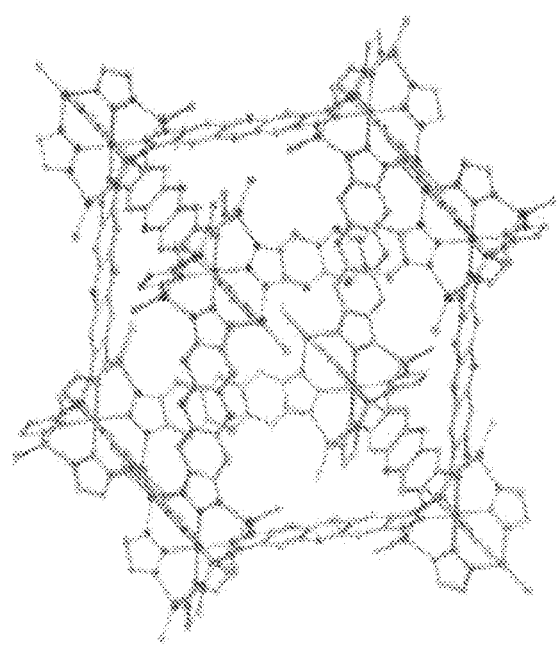
FIG. 1A-FIG. 1D show simulated structures of a non-limiting MOF, according to some embodiments.
Figure 1B:
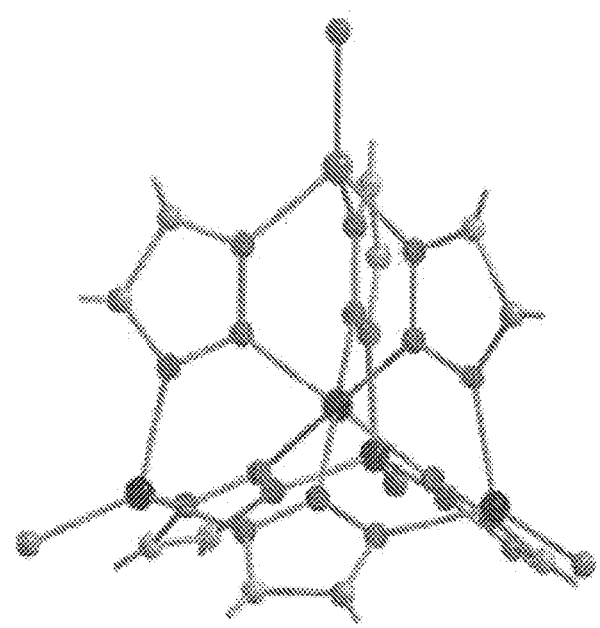
Figure 1C:
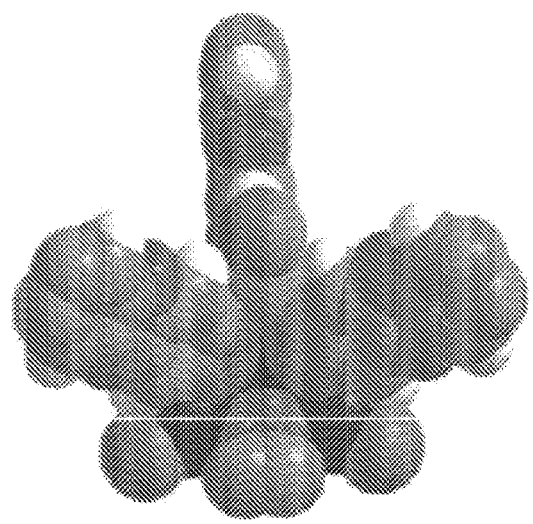
Figure 1D:
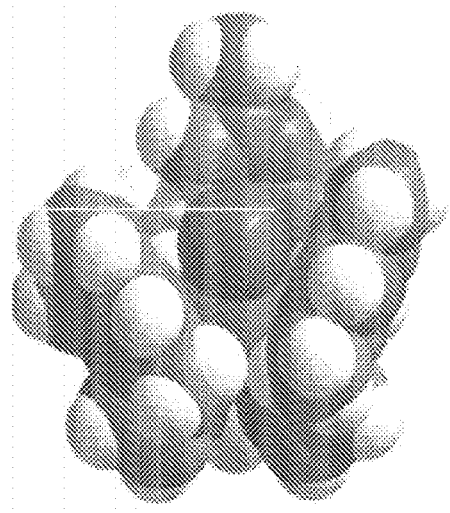

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

Compositions and methods comprising metal organic frameworks (MOFs) and related uses are generally provided. In some embodiments, a MOF comprises a plurality of metal ions, each coordinated with at least one ligand, wherein each ligand comprises at least two unsaturated N-heterocyclic aromatic groups.

The term "metal-organic framework" is given its ordinary meaning in the art and refers to a one-, two-, or three-dimensional coordination polymer including metal ions and ligands which function as organic structural units, wherein a portion of the metal ions are each chemically bonded to at least one bi-, tri- or poly-dentate organic structural unit. The metal ions, in addition to being coordinated with at least one ligand, may also be bound to one or more auxiliary ligands, as described in more detail herein.

The MOFs described herein may be utilized in a wide variety of applications. In some embodiments, the MOFs may be utilized as a catalyst. For example, in some embodiments, the MOFs may be utilized as a catalyst for olefin oligomerization or olefin dimerization. In a particular embodiment, the MOF may be utilized as a catalyst for ethylene dimerization (e.g., to form 1-butene).

In some embodiments, the catalyst is a heterogeneous catalyst. The term "heterogeneous catalyst" will be understood by those of ordinary skill in the art and generally refers to a catalyst in solid state catalyzing a reaction which is fully or partly run in another phase, such as a solvent phase or gaseous phase. In some embodiments, the MOFs described herein are utilized in a solid state, for example, as a solid dispersed in a solution. One non-limiting advantage to heterogeneous catalysts is the catalyst may generally be easily separated from a reaction mixture. In some embodiments, the catalyst (e.g., the heterogeneous catalyst) is a single site catalyst. The term "single site catalyst" will be understood by those of ordinary skill in the art and generally refers to a catalyst that has only a single type of kinetically active site. For example, for the MOFs described herein, a single type of metal ion for each MOF may act as the catalytic site(s).

The MOFs described herein are particularly advantageous as catalysts for the oligomerization (e.g., dimerization) of olefins such as ethylene. In some embodiments, the MOFs described herein have high turnover frequencies (e.g., greater than about 12,400 moles of ethylene per mole of active metal ion at room temperature under 30 bar of ethylene, greater than about 21,600 moles of ethylene per mole of active metal ion at room temperature under 30 bar of ethylene), high selectivity (e.g., greater than about 95% for butenes), and/or long catalyst lifetimes as compared to traditional olefin catalysts. In some embodiments, the TOF is about 27,000 with a selectivity of 96% for 1-butene at 50 bar of ethylene. In some embodiments, the TOF is about 41,500 with a selectivity of 96% for 1-butene at 50 bar of ethylene. The MOF catalysts described herein may generally be used in any reactor suitable for the oligomerization of olefins. While much of the description herein relates to the dimerization of ethylene, those skilled in the art would understand, based upon the teachings of this specification, that other olefins such as propylene, 1-butene, or 1-pentene may also be oligomerized by catalysis with such MOFs.

Those of ordinary skill in the art will be aware of suitable systems and methods for utilizing a MOF described herein for catalysis. For example, the MOF may be loaded into a reactor for use as an olefin oligomerization catalyst. Olefins (e.g., ethylene, propylene, or the like) may be introduced into the reactor, wherein the olefin oligomerizes upon exposure to the catalyst. Optionally, the reactor may contain one or more solvents (e.g., an organic solvent) and/or one or more additives (e.g., alkylaluminum). The reactor may be operated at any suitable temperature and/or pressure. In some embodiments, the reactor may be operated until a high fraction (e.g., greater than about 80%, greater than about 90%, greater than about 95%, or more) of the desired oligomer (e.g., butene) is produced. In some embodiments, the reactor is operated at or near atmospheric pressure. In other embodiments, the reactor is operated at elevated pressures (e.g., under an atmosphere of ethylene).

In some embodiments, oligomerization of an olefin is conducted (e.g., the formation of butene from ethylene) in the presence of the MOF and an additive. The presence of the additive, in some cases, may increase the turnover frequency and/or the selectivity of the oligomerization carried out in the presence of the MOF (e.g., for butene) as compared to the turnover frequency and/or the selectivity in the absence of the additive. In some embodiments, the additive is an alkylaluminum compound. Non-limiting examples of alkylaluminum compounds include aluminoxanes (e.g., methylaluminoxane, modified methylaluminoxane) ethylaluminum dichloride, diethylaluminum chloride, triethylaluminum, and trimethylaluminum. In an exemplary embodiments, the additive is methylaluminoxane. In some embodiments, the additive is an alkyl magnesium halide (e.g., ethyl magnesium bromide). In some embodiments, the additive is an alkyllithium compound (e.g., methyllithium). The additive may be provided in any suitable amount. In some embodiments, the ratio of moles of additive to moles of active metal center (e.g., $Ni^{+2}$) is between 1 and 1000, or between 1 and 500, or between 1 and 250, or between 1 and 100, or between 50 and 500, or between 50 and 400, or between 50 and 300, or between 50 and 200, or between 50 and 150, or about 1, about 2, about 5, about 10, about 25, about 50, or about 100.

The oligomerization may be conducted at any suitable temperature or pressure. For example, in some cases, oligomerization in the presence of the MOF may be conducted at a temperature of at least about 0° C., at least about 25° C., at least about 50° C., or at least about 100° C. In certain embodiments, oligomerization in the presence of the MOF may be conducted at a temperature of less than or equal to about 150° C., less than or equal to about 100° C., less than or equal to about 50° C., or less than or equal to about 25° C. Combinations of the above-referenced ranges are also possible (e.g., between about 0° C. and about 150° C.). Other ranges are also possible.

In some embodiments, oligomerization in the presence of the MOF is conducted at a pressure of at least about 15 bar, at least about 30 bar, or at least about 50 bar. In certain embodiments, oligomerization in the presence of the MOF is conducted at a pressure of less than or equal to about 75 bar, less than or equal to about 50 bar, or less than or equal to about 30 bar. Combinations of the above-referenced ranges are also possible (e.g., between about 15 bar and about 75 bar). Other ranges are also possible. Those skilled in the art would be capable of selecting suitable combinations of temperatures and pressures for the oligomerization of olefins based upon the teachings of the specification.

In some embodiments, the MOFs described herein may catalyze the formation of butene from ethylene with high selectivity. For example, in some embodiments, butene is formed in the presence of a MOF with a selectivity of at least about 80%, at least about 85%, at least about 90%, at least about 95%, at least about 97%, at least about 98%, at least about 99%, at least about 99.5%, at least about 99.8%, or at least about 99.9% for butene. In certain embodiments, butene is formed in the presence of a MOF with a selectivity of 100% for butene.

In certain embodiments, butene is formed with a high weight percentage of 1-butene versus the total amount of butenes. That is to say, the MOFs described herein may also catalyze the formation of 1-butene from ethylene with a high selectivity. In some embodiments, at least about 80 wt %, at least about 85 wt %, at least about 90 wt %, at least about 95 wt %, at least about 97 wt %, at least about 98 wt %, at least about 99 wt %, at least about 99.5 wt %, at least about 99.8 wt, or at least about 99.9 wt % of amount of butene formed from ethylene in the presence of the MOFs described herein is 1-butene.

Those of ordinary skill in the art will be aware of methods and techniques for determining selectivity. The selectivity of a reaction for 1-butene may be determined by determining the percent by weight of 1-butene based on total amount of products (e.g., butenes, hexenes, octenes, etc.) produced. For example, gas chromatography may be used to determining the weight percentage of butene versus the total amount of product produced and/or the total weight percentage of 1-butene versus the total amount of butenes produced.

In certain embodiments, the MOF may catalyze the formation of butene with a high turnover frequency. Turnover frequency, as used herein, refers to the number of moles of ethylene consumed per moles of active metal centers in the MOF. For example, in some embodiments, wherein the active metal center is a nickel ion, the TOF refers to the number of moles of ethylene consumed per mole of nickel. In some embodiments, butenes (and 1-butene) is formed in the presence of the MOF at a turnover frequency of at least about 12,000, at least about 12,500, at least about 14,000, at least about 15,000, at least about 16,000, at least about 17,500, at least about 18,000, at least about 20,000, at least about 21,000, at least about 22,000, at least about 25,000, at least about 27,000, or at least about 30,000, at least about 35,000, or at least about 41,500 per hour per moles of active metal centers (e.g., nickel). In certain embodiments, butene (and 1-butene) is formed in the presence of the MOF at a turnover frequency of less than or equal to about 40,000, less than or equal to about 30,000, less than or equal to about 25,000, less than or equal to about 20,000, less than or equal to about 18,000, less than or equal to about 16,000, less than or equal to about 15,000, or less than or equal to about 14,000 per hour per moles of active metal centers (e.g., nickel). Combinations of the above referenced ranges are also possible (e.g., between about 12,000 and about 40,000 per hour per moles of active metal centers (e.g., nickel)).

In some embodiments, the TOF is determined per hour at 25° C. and 50 bar. The number of moles of ethylene converted can be determined, for example, using gas chromatography after an hour of reacting the ethylene with the metal ion-containing MOF at 25° C. Those of ordinary skill in the art will be aware of methods and systems for determining the number of moles of active metal centers. For example, in embodiments wherein the active metal center is nickel and the MOF also comprises zinc, number of moles of nickel may be determined based at least in part on the ratio of nickel to zinc (e.g., based on the structure of the MOF) and the weight of the MOF used.

In some embodiments, the MOF may catalyze the formation of butene or 1-butene with a selectivity of at least about 50%, or 60%, or 70%, or 75%, or 80%, or 85%, or 90%, or 95% and a turnover frequency of at least about 12,500 per hour per moles of active metal centers (e.g., nickel). In some embodiments, the MOF may catalyze the formation of butene or 1-butene with a selectivity of at least about 50%, or 60%, or 70%, or about 75%, or 80%, or 85%, or 90%, or 95% and a turnover frequency of at least about 15,000 per hour per moles of active metal centers (e.g., nickel). In some embodiments, the MOF may catalyze the formation of butene or 1-butene with a selectivity of at least about 50%, or 60%, or 70%, or about 75%, or 80%, or 85%, or 90%, or 95% and a turnover frequency of at least about 17,500 per hour per moles of active metal centers (e.g., nickel). In some embodiments, the MOF may catalyze the formation of butene or 1-butene with a selectivity of at least about 50%, or 60%, or 70%, or about 75%, or 80%, or 85%, or 90%, or 95% and a turnover frequency of at least about 20,000 per hour per moles of active metal centers (e.g., nickel). In some embodiments, the MOF may catalyze the formation of butene or 1-butene with a selectivity of at least about 50%, or 60%, or 70%, or about 75%, or 80%, or 85%, or 90%, or 95% and a turnover frequency of at least about 22,500 per hour per moles of active metal centers (e.g., nickel). In some embodiments, the MOF may catalyze the formation of butene or 1-butene with a selectivity of at least about 50%, or 60%, or 70%, or about 75%, or 80%, or 85%, or 90%, or 95% and a turnover frequency of at least about 25,000 per hour per moles of active metal centers (e.g., nickel). In some embodiments, the MOF may catalyze the formation of butene or 1-butene with a selectivity of at least about 50%, or 60%, or 70%, or about 75%, or 80%, or 85%, or 90%, or 95% and a turnover frequency of at least about 27,000 per hour per moles of active metal centers (e.g., nickel). In some embodiments, the MOF may catalyze the formation of butene or 1-butene with a selectivity of at least about 50%, or 60%, or 70%, or about 75%, or 80%, or 85%, or 90%, or 95% and a turnover frequency of at least about 30,000 per hour per moles of active metal centers (e.g., nickel). In some embodiments, the MOF may catalyze the formation of butene or 1-butene with a selectivity of at least about 50%, or 60%, or 70%, or about 75%, or 80%, or 85%, or 90%, or 95% and a turnover frequency of at least about 35,000 per hour per moles of active metal centers (e.g., nickel). In some embodiments, the MOF may catalyze the formation of butene or 1-butene with a selectivity of at least about 50%, or 60%, or 70%, or about 75%, or 80%, or 85%, or 90%, or 95% and a turnover frequency of at least about 41,500 per hour per moles of active metal centers (e.g., nickel).

In some embodiments, a MOF comprises a plurality of metal ions, each coordinated with at least one ligand comprising at least two unsaturated N-heterocyclic aromatic groups. In some embodiments, at least some of the metal ions are associated with two, three, or four ligands, and each of those ligands are individually associated with one, two, three, or four metal ions. In some embodiments, at least some of the metal ions are associated with two ligands, and each of those ligand is individually associated with two metal ions. In some embodiments, at least some of the metal ions are associated with three ligands, and each of those ligand is individually associated with three metal ions. In some embodiments, at least some of the metal ions are associated with four ligands, and each of those ligand is individually associated with two metal ions. In some embodiments, a ligand is charged. In some embodiments, a ligand has a charge of (−1), or (−2), or (−3), or (−4). In some embodiments, a ligand has a charge of (−2).

In some cases, each metal ion is coordinated with at least two ligands, at least three ligands, or at least four ligands. For example, in some embodiments, the MOF comprises a plurality of metal ions associated with at least two triazolates, at least three triazolates, or at least four triazolates. Other non-limiting examples of suitable ligands are described in detail herein. In some embodiments, the plurality of metal ions may be selected from the group consisting of $Ni^{2+}$, $Ti^{3+}$, $Ti^{4+}$, $Cr^{2+}$, $Cr^{3+}$, $Mn^{2+}$, $Fe^{3+}$, $Fe^{2+}$, $Co^{2+}$, $Cu^{2+}$, and $Zn^{2+}$, or combinations thereof.

Any suitable metal ion may be employed. Each metal ion may be monovalent, divalent, trivalent, or tetravalent. In some embodiments, a least one type of metal ion is a monovalent metal ion. In some embodiments, each metal ion is a monovalent metal ion. Non-limiting examples of monovalent metal ions are $Ag^+$, $Cu^+$, and $Au^+$. In some embodiments, at least one type of metal ion is a divalent metal ion. In some embodiments, the metal ion is a divalent metal ion. Non-limiting examples of monovalent metal ions are $Mg^{2+}$, Mn$^{2+}$, Fe$^{2+}$, Co$^{2+}$, Ni$^{2+}$, Cu$^{2+}$, Pd$^{2+}$, Pt$^{2+}$, Ru$^{2+}$, Cd$^{2+}$, Zn$^{2+}$, Pb$^{2+}$, Hg$^{2+}$, V$^{2+}$, and Cr$^{2+}$. In some cases, the metal ion is Ni$^{+2}$. In some embodiments, at least one type of metal ion is a divalent metal ion. In some embodiments, the metal ion is a trivalent metal ion. Non-limiting examples of trivalent metal ions are Fe$^{3+}$, V$^{3+}$, Ti$^{3+}$, Sc$^{3+}$, Al$^{3+}$, In$^{3+}$, Ga$^{3+}$, Mn$^{3+}$, Co$^{3+}$, and Cr$^{3+}$. In some embodiments, at least one type of metal ion is a tetravalent metal ion. In some embodiments, the metal ion is a tetravalent metal ion. A non-limiting examples of tetravalent metal ion is Ti$^{4+}$.

In some embodiments, the MOF comprises a plurality of a first type of metal ion and a plurality of a second type of metal ion. In some cases, the first type of metal is Ni$^{2+}$. In some embodiments, the second type of metal ion is Zn$^{2+}$. In some embodiments, each MOF comprises a single metal ion of the first type. In some embodiments, each MOF comprises more than one of the first type of metal ion. In some embodiments, one or more of the first type of metal ion are the active metal centers for catalysis. In some embodiments, only a single first type of metal ion is an active metal center for catalysis.

In an exemplary embodiment, the MOF catalyst comprises a plurality of metal ions which are each Ni$^{2+}$. In some embodiments, the MOF comprises a plurality of Ni$^{+2}$ ions and a plurality of a second type of metal ion. In such embodiments, the Ni$^{+2}$ metal centers are the active metal centers for catalysis. In another exemplary embodiment, the MOF catalyst comprises a plurality of metal ions selected from Ni$^{2+}$ and Zn$^{2+}$. For example, in some embodiments, the MOF catalyst comprises a first metal ion comprising Ni$^{2+}$ and a second metal ion comprising Zn$^{2+}$, where the first metal ion and the second metal ion are each coordinated with at least one ligand comprising a triazolate.

In some embodiments, more than one type of metal ion may be employed, for example, a first type of metal ion and a second type of metal ion. In some cases, the first type of metal ion and the second type of metal ion may have the same valency. For example, the first type of metal ion may be a first type of divalent metal ion and the second type of metal ion may be a second different type of divalent metal ion. The two or more types of metal ions may be provided in any suitable ratio.

In some embodiments, a metal ion may be associated with one or more one auxiliary ligands. In some cases, the one or more auxiliary ligand may be found above and/or below the metal ion (e.g., as apical ligands). An auxiliary ligand may or might not be charged. Non-limiting examples of auxiliary ligands include halides (e.g., chlorine, fluorine, bromine, iodine), other salts (e.g., alkyl (e.g., —CH$_3$), allyl, nitrite, sulfite, chloride, fluoride, bromide, iodide, triflate, BF$_4$, PF$_6$, NO$_3^-$, SO$_4^{2-}$, ClO$_4^-$, nitrate, carbonate, sulfonate, etc.), and coordinating solvents (e.g., water, pyridine, tetrahydrofuran, diethyl ether, tetrahydrofuran, ammonia, toluene, benzene, etc.).

In an exemplary embodiment, the MOF comprises Ni (e.g., as Ni$^{+2}$), a plurality of second type of metal ions (e.g., Zn$^{+2}$), wherein the Ni metal center is associated with three unsaturated N-heterocyclic aromatic groups and optionally an anion. For example, the MOF or a portion of the MOF may comprise the structure:

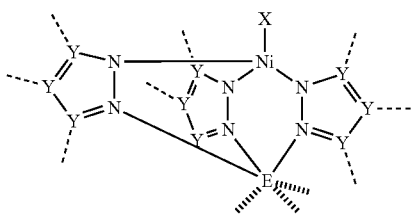

wherein each heteroaromatic ring is a portion of a ligand (as indicated by the dashed lines), each Y is independently N or C, E is an ion (e.g., a second type of metal ion, optionally bound to one or more additional ligands and indicated by the III on lines), and X is an anion. In some embodiments, E is a second type of metal ion. The second type of metal ion may or might not be nickel. In some cases, the second type of metal ion is zinc. In some embodiments structure, E is coordinated with three unsaturated N-heterocyclic aromatic groups. In some embodiments, the MOF or a portion of the MOF comprises the structure:

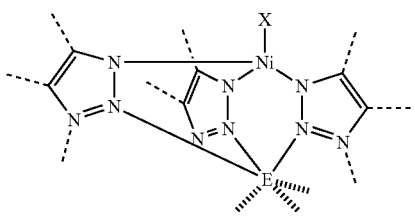

wherein E and X are as described above.

In some embodiments, X may be absent in all of or a portion of the MOF. For example, in a non-limiting example, a portion of the MOF may comprise the structure:

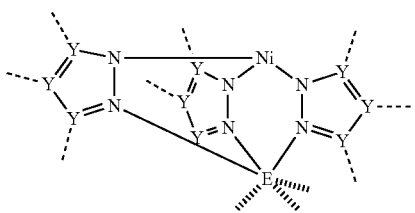

wherein each heteroaromatic ring is a portion of a ligand, each Y is independently N or C, M is a metal ion selected from the group consisting of Ni$^{2+}$, Ti$^{3+}$, Cr$^{2+}$, Cr$^{3+}$, Mn$^{2+}$, Fe$^{2+}$, Co$^{2+}$, Cu$^{2+}$, Zn$^{2+}$, and X is a suitable anion.

In some embodiments, E may be absent in a portion of or all of the MOF. For example, in a non-limiting example, a portion of the MOF may comprise the structure:

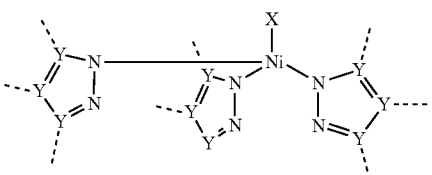

wherein each heteroaromatic ring is a portion of a ligand, each Y is independently N or C, and X is a suitable anion.

It should be understood that while the ligands depicted above contain 5-membered rings, a heterocycle of any ring size may be substituted in the place of any or all of the ligands coordinated to the metal ion. Furthermore, the MOF may comprise one or more of the above structures. For example, in some embodiments, a significant portion of the MOF comprises both E and X and at least a portion of the MOF does not comprise the E and/or X.

In some embodiments, $M^2$ is bound to additional ligands comprising N-heterocyclic aromatic groups. In some embodiments, $M^2$ is bound by six ligands comprising N-heterocyclic aromatic groups. In some embodiments, the ligand comprising the N-heterocyclic aromatic group has a structure as in Formula (I):

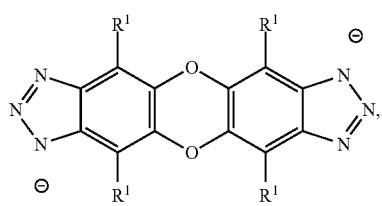
(I)

wherein each $R^1$ is the same or different and is selected from the group consisting of hydrogen, -alkyl, —NO$_2$, —R', —F, —Cl, —Br, —I, —CN, —NC, —SO$_3$R', —SO$_3$H, —OR', —OH, —SR', —SH, —PO$_3$R', —PO$_3$H, —CF$_3$, —NR'$_2$, —NHR', and —NH$_2$, and each R' is the same or different and is optionally substituted alkyl or optionally substituted aryl. In some embodiments, $M^2$ is bound to six unsaturated N-heterocyclic aromatic groups having a structures as in Formula (I). In some embodiments, each $R^1$ is hydrogen. In some embodiments, the ligand comprising the N-heterocyclic aromatic group

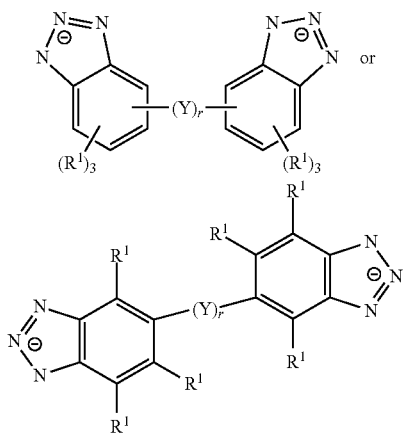

wherein each $R^1$ is the same or different and is selected from the group consisting of hydrogen, -alkyl, —NO$_2$, —R', —F, —Cl, —Br, —I, —CN, —NC, —SO$_3$R', —SO$_3$H, —OR', —OH, —SR', —SH, —PO$_3$R', —PO$_3$H, —CF$_3$, —NR'2, —NHR', and —NH$_2$, wherein each R' is the same or different and is optionally substituted alkyl or optionally substituted aryl, wherein each Y is independently alkylene, heteroalkylene, arylene, heteroarylene, —O—, —C(=O), —S—, and r is 0, 1, 2, or 3. In some embodiments, r is 0 (e.g., so that the two aryl rings are directly bound via a bond). In some embodiments, each $R^1$ is hydrogen. In some embodiments, r is 0 and each $R^1$ is hydrogen. In some embodiments, the ligand has the structure:

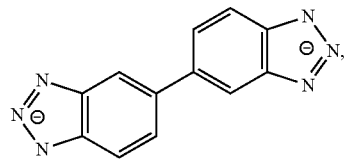

also referred to herein as "bibta". In some embodiments, E is Ti$^{3+}$, Cr$^{2+}$, Cr$^{3+}$, Mn$^{2+}$, Fe$^{2+}$, Co$^{2+}$, Cu$^{2+}$, and Zn$^{2+}$, and each X is any suitable anion or optionally absent. Non-limiting examples of suitable anions include alkyl (e.g., —CH$_3$), allyl, nitrite, sulfite, chloride, fluoride, bromide, iodide, triflate, BF$_4$, PF$_6$, NO$_3^-$, SO$_4^{2-}$, and ClO$_4^-$.

As described above, generally, the MOF comprises at least one ligand comprising at least two unsaturated N-heterocyclic aromatic groups. In some embodiments, at least one ligand comprises two unsaturated N-heterocyclic aromatic groups. In some embodiments, at least one ligand comprises three unsaturated N-heterocyclic aromatic groups. In some embodiments, each ligand comprises two unsaturated N-heterocyclic aromatic groups. In some embodiments, each ligand comprises three unsaturated N-heterocyclic aromatic groups. In some embodiments, each ligand comprises four unsaturated N-heterocyclic aromatic groups.

The unsaturated N-heterocyclic aromatic group may be selected from any suitable group. Non-limiting examples include pyrrolate, pyrazolate, triazolate, imidazolate, oxazolate, tetrazolate, and pyridinate. Other non-limiting examples include thiazolate, oxadiazolate, purinate, quinolonate, and indolate.

In some embodiments, the unsaturated N-heterocyclic aromatic groups are selected from the group consisting of pyrazolate, triazolate, imidazolate, and tetrazolate. In some embodiments, the unsaturated N-heterocyclic aromatic groups are selected from the group consisting of pyrazolate, pyridinate, imidazolate, triazolate, and tetrazolate. In some embodiments, the unsaturated N-heterocyclic aromatic groups are selected from the group consisting of imidazolate, imidazolate, triazolate, and tetrazolate. In some embodiments, the unsaturated N-heterocyclic aromatic groups are pyrazolates. In certain embodiments, the unsaturated N-heterocyclic aromatic groups are triazolates. Non-limiting examples of triazolate include 1,2,4-triazolate and 1,2,3-triazolate.

For example, in some embodiments, the at least one ligand comprises two or more triazolate, three or more triazolate, or four or more triazolate. In some embodiments, the at least one ligand comprises two triazolates. In some embodiments, the ligand comprises three triazolate. Other N-heterocyclic aromatic groups described herein, and/or combinations of two or more N-heterocyclic aromatic groups described herein, are also possible. For example, in some embodiments, the at least one ligand comprises at least one triazolate and at least one tetrazolate (e.g., one triazolate and one tetrazolate, two triazolates and one tetrazolate, two triazolates and two tetrazolates, etc.). Other combinations are possible.

In some embodiments, the at least one ligand comprises at least two unsaturated N-heterocyclic aromatic groups arranged about an organic core. The organic core of the ligand comprising at least two unsaturated N-heterocyclic aromatic groups may be any suitable core. In some embodiments, the core is aromatic. Generally, the core comprises a rigid structure formed from fused aryl and/or heteroaryl rings. In some embodiments, the organic core comprises a plurality of fused aryl and/or heteroaryl rings. In some cases, the organic core comprises a plurality of fused aryl rings. In some cases, the organic core comprises one or more of benzyl, thiophenyl, carbazolyl, pyrrolyl, indolyl, and furanyl.

In some embodiments, the at least one ligand comprises a structure as in:

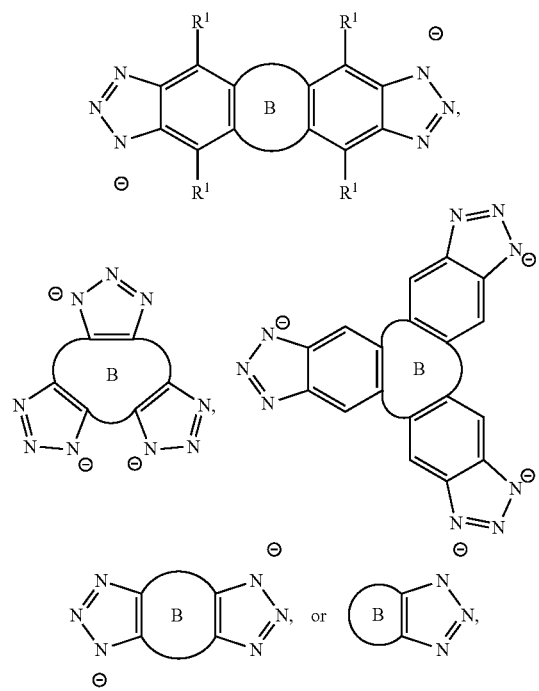

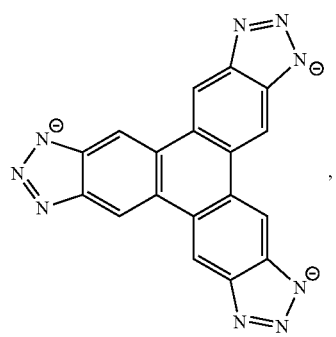

wherein B is an aromatic or heterocyclic core (e.g., comprising one or more aromatic rings, e.g. B can be biphenyl), wherein each $R^1$ is the same or different and is selected from the group consisting of hydrogen (—H), -alkyl (e.g., —CH$_3$), —NO$_2$, —R', —F, —Cl, —Br, —I, —CN, —NC, —SO$_3$R', —SO$_3$H, —OR', —OH, —SR', —SH, —PO$_3$R', —PO$_3$H, —CF$_3$—, —NR'$_2$, —NHR', and —NH$_2$, wherein each R' is the same or different and is optionally substituted alkyl or optionally substituted aryl. In some embodiments, each $R^1$ is the same and is hydrogen. Non-limiting examples of such ligands include:

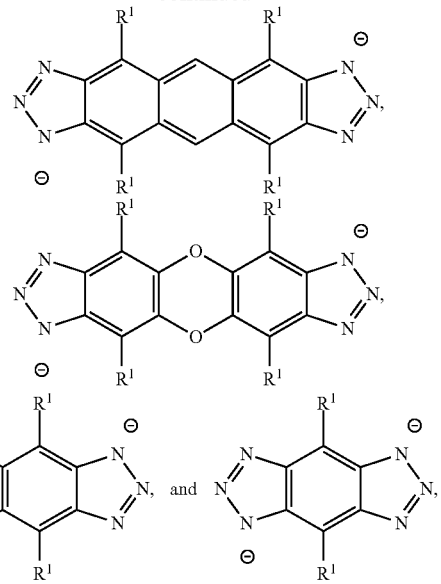

wherein each $R^1$ is the same or different and is selected from the group consisting of hydrogen, -alkyl, —NO$_2$, —R', —F, —Cl, —Br, —I, —CN, —NC, —SO$_3$R', —SO$_3$H, —OR', —OH, —SR', —SH, —PO$_3$R', —PO$_3$H, —CF$_3$, —NR'$_2$, —NHR', and —NH$_2$, wherein each R' is the same or different and is optionally substituted alkyl or optionally substituted aryl. In some embodiments, each $R^1$ is the same and hydrogen.

In certain embodiments, the ligand comprises the structure as in:

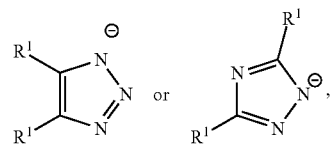

wherein each $R^1$ is the same or different and is selected from the group consisting of hydrogen, -alkyl, —NO$_2$, —R', —F, —Cl, —Br, —I, —CN, —NC, —SO$_3$R', —SO$_3$H, —OR', —OH, —SR', —SH, —PO$_3$R', —PO$_3$H, —CF$_3$, —NR'$_2$, —NHR', and —NH$_2$, wherein each R' is the same or different and is optionally substituted alkyl or optionally substituted aryl.

In some embodiments, the ligand comprises the structure:

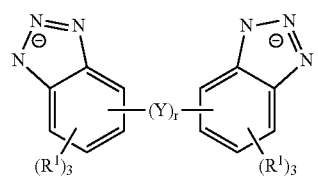

wherein each $R^1$ is the same or different and is selected from the group consisting of hydrogen, -alkyl, —NO$_2$, —R', —F, —Cl, —Br, —I, —CN, —NC, —SO$_3$R', —SO$_3$H, —OR', —OH, —SR', —SH, —PO$_3$R', —PO$_3$H, —CF$_3$, —NR'$_2$, —NHR', and —NH$_2$, wherein each R' is the same or different and is optionally substituted alkyl or optionally substituted aryl, wherein each Y is independently alkylene, heteroalkylene, arylene, heteroarylene, —O—, —C(=O), —S—, and r is 0, 1, 2, or 3. In some embodiments, r is 0. In some embodiments, each R¹ is hydrogen. In some embodiments, the ligand has the structure:

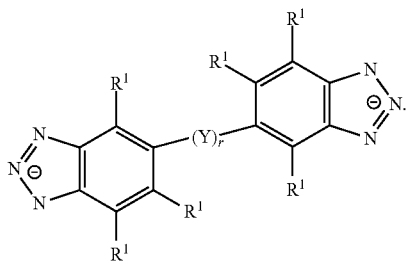

In some embodiments, r is 0. In some embodiments, each R¹ is H. In some embodiments, r is 0 and each R¹ is hydrogen.

In some embodiments, more than one type of ligand comprising at least two unsaturated N-heterocyclic aromatic groups may be employed, for example, a first type of ligand and a second type of ligand. The two or more types of ligands may be provided in any suitable ratio. As described herein, the ligand may comprise any combination of unsaturated N-heterocyclic aromatic groups (e.g., at least one triazolate; a combination of triazolates and tetrazolates; at least one tetrazolate, etc.) In some embodiments, following synthetic modification of a MOF or a precursor ligand which is to be utilized to form a MOF, a mixture of types of ligands (or precursor ligands) may be present. For example, the ligands within the MOF or a plurality of precursor ligands that will be used to form a MOF may be synthetically modified (e.g., oxidized) and only a portion of the substituents of the ligands or precursor ligands may be altered. Thus, the ligands within the MOF or the precursor ligands used to form the MOF may comprise a number of different substitution patterns. As a non-limiting example, if the ligand (or precursor ligand) comprises two substituents that are targeted to be modified, upon modification of a plurality of the ligands, for each ligand within the plurality, both substituents may be modified, or only one substituent may be modified, or neither substituent may be modified. Thus, the plurality of ligands may comprise some ligands with both substituents modified, some ligands with only one substituent modified, and some ligands with neither substituent modified. The MOFs may be synthesized using methods known in the art (e.g., see *Chem. Eur. J.* 2011, 17, 1837-1848; *Chem. Eur. J.* 2015, 21, 8188-8199). For example, in some cases, a method of synthesizing a MOF comprises exposing a plurality of metal ions to a plurality of precursor ligands to form a MOF comprising a portion of the plurality of metal ions each coordinated with at least one ligand, wherein the at least one ligand comprises at least two unsaturated N-heterocyclic aromatic groups arranged about an organic core. Non-limiting examples of ligands comprises at least unsaturated N-heterocyclic aromatic groups arranged about an organic core are described herein. In some embodiments, the metal ion is provided as a salt, and the at least one precursor ligand comprises at least two N-heterocyclic aromatic groups which, during the course of the reaction are deprotonated to form the corresponding ligand (e.g., comprising unsaturated N-heterocyclic aromatic groups). For example, the precursor ligand may be deprotonated to have a charge of (−1), or (−2), or (−3), or (−4). Exemplary precursor ligands are described herein.

In some embodiments, an MOF comprising at least a first type of metal ion and a second type of metal ion may be prepared by metal exchange of a substantially similar MOF comprising only a single type of metal ion. In some embodiments, the metal exchange may be carried out by adding the first type of metal ion to solution comprising the MOF comprising only the second type of metal ion. For example, an MOF comprising zinc ions may be exposed to a plurality of a first type of metal ions (e.g., in solution) and at least one zinc ion may be exchanged by a first type of metal ion (e.g., $Ni^{2+}$). In some embodiments, only one of the second type of metal ions is exchanged with the first type of metal ion. In some embodiments, one or less of the second type of metal ions is exchanged with the first type of metal ion. In other embodiments, more than one of the second type of metal ions is replaced with the first type of metal ion.

In some embodiments, following synthesis of the MOF, the MOF may be modified. For example, the ligands of the MOF may be modified to include one or more functional groups and/or the one or more of the functional groups of the ligand may be modified. The ability to modify in the MOF following synthesis of the MOF is beneficial as the properties of the MOFs may be more readily tuned. In some embodiments, the MOF is modified to include hydrophilic groups. The MOF may be modified using any suitable technique. In some embodiments, the MOF is exposed to oxidative conditions to associate new functional groups and/or modify currently present functional groups that are present on the ligand of the MOF. As a non-limiting example, a ligand of the MOF may comprise one or more alkyl sulfide groups, and the MOF may be exposed to oxidizing conditions (e.g., dimethyldioxirane) to modify the alkyl sulfide groups into alkyl sulfoxides or alkyl ethyl sulfones groups.

In some embodiments, following synthesis of the MOF, one or more of the metal ions may be exchanged. For example, an MOF comprising zinc ions may be exposed to a plurality of nickel ions, and at least one zinc ion may be replaced by a nickel ion.

In some embodiments, the MOFs formed may comprise little or no excess metal ions. That is, the MOF comprises essentially no metal ions which are not coordinated with a ligand comprising at least two unsaturated N-heterocyclic aromatic groups (i.e., "free metal ions"). In some embodiments, the MOF comprises less than about 0.5 wt %, or less then about 0.4 wt %, or less then about 0.3 wt %, or less than about 0.2 wt %, or less then about 0.1 wt %, or less than about 0.05 wt %, or less than about 0.03 wt %, or less than about 0.02 wt %, or less than about 0.01 wt %, or less than about 0.005 wt %, or less than about 0.001 wt % of free metal ions. Those of ordinary skill in the art will be aware of methods for determining the amount of free metal ions, for example, using XPS.

In some embodiments, each precursor ligand comprises two N-heterocyclic aromatic groups. In some embodiments, each precursor ligand comprises three N-heterocyclic aromatic groups. In some embodiments, each precursor ligand comprises four N-heterocyclic aromatic groups. The N-heterocyclic aromatic group for the precursor ligand may be selected from any suitable group. Non-limiting examples are pyrrole, pyrazole, triazole, imidazole, and tetrazole. In some embodiments, the N-heterocyclic aromatic groups are selected from the group consisting of pyrazole, triazole, imidazole, and tetrazole. In some embodiments, the N-heterocyclic aromatic groups are selected from the group consisting of pyrazole, imidazole, and tetrazole. In some embodiments, the N-heterocyclic aromatic groups are pyrazoles. The organic core of the precursor ligand comprising at least two N-heterocyclic aromatic groups may be as described here.

In some embodiments, each precursor ligand has the structure:

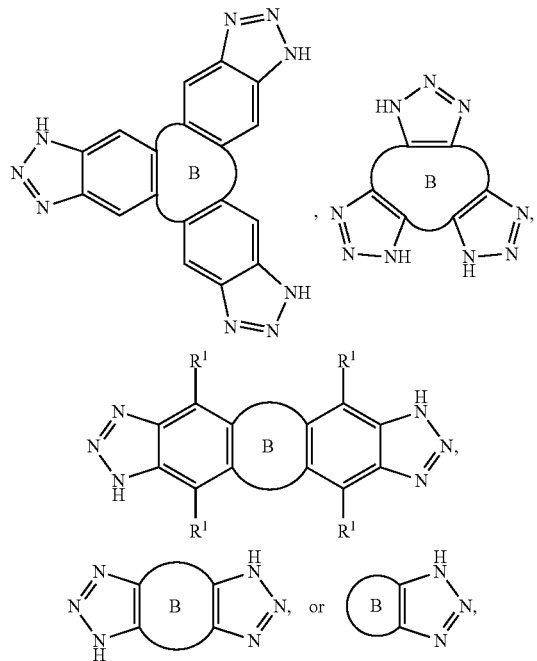

wherein B is an aromatic or heterocyclic core, wherein each R¹ is the same or different and is selected from the group consisting of hydrogen, -alkyl, —NO₂, —R', —F, —Cl, —Br, —I, —CN, —NC, —SO₃R', —SO₃H, —OR', —OH, —SR', —SH, —PO₃R', —PO₃H, —CF₃, —NR'₂, —NHR', and —NH₂, wherein each R' is the same or different and is optionally substituted alkyl or optionally substituted aryl. In some embodiments, each R¹ is the same and is hydrogen. Non-limiting examples of such ligands include:

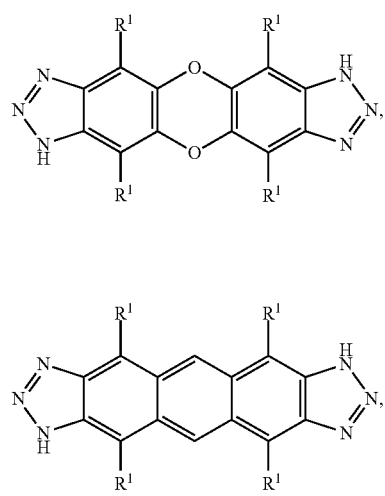

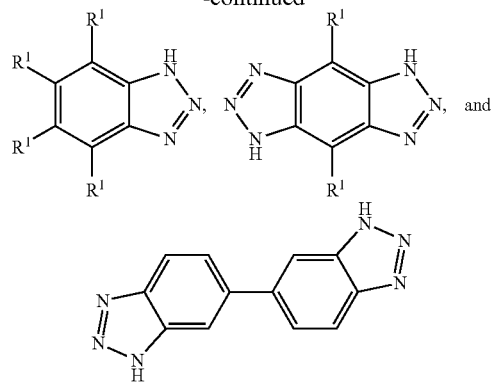

wherein each R¹ is the same or different and is selected from the group consisting of hydrogen, —NO₂, —R', —F, —Cl, —Br, —I, —CN, —NC, —SO₃R', —SO₃H, —OR', —OH, —SR', —SH, —PO₃R', —PO₃H, —CF₃, —NR'₂, —NHR', and —NH₂, wherein each R' is the same or different and is optionally substituted alkyl or optionally substituted aryl. In some embodiments, each R¹ is the same and hydrogen.

In some embodiments, each precursor ligand has a structure as in:

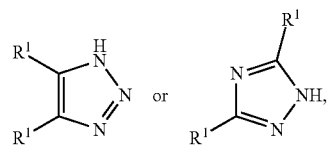

wherein each R¹ is the same or different and is selected from the group consisting of hydrogen, —NO₂, —R', —F, —Cl, —Br, —I, —CN, —NC, —SO₃R', —SO₃H, —OR', —OH, —SR', —SH, —PO₃R', —PO₃H, —CF₃, —NR'₂, —NHR', and —NH₂, wherein each R' is the same or different and is optionally substituted alkyl or optionally substituted aryl. In a particular embodiment, each R¹ is the same and hydrogen.

The metal ion and the ligand may be provided in any suitable amounts. In some embodiments, the mole ratio of the metal ion to the ligand may be based upon the coordination of the metal ion to the ligand. For example, in embodiments, where the ligand is coordinated with three metal ions, and each metal ion is associated with two ligands, the mole ratio of the metal ion to the ligand may be at least 3:2. As another example, in embodiments, where the ligand is coordinated with two metal ions, and each metal ion is associated with one ligand, the mole ratio of the metal ion to the precursor ligand may about 2:1. In some embodiments, the ligand is providing in slight mole excess.

In some embodiments, the metal ions are provided as a salt. Non-limiting examples of salts chloride, fluoride, bromide, iodide, triflate, $BF_4$, $PF_6$, $NO_3^-$, $SO_4^{2-}$, and $ClO_4^-$ salts. In some cases, the salt is $SO_4^{2-}$.

Any suitable solvent may be utilized in the synthetic methods of forming the MOFs described herein. Non-limiting examples of solvents include water, methanol, ethanol, propanol, benzene, p-cresol, toluene, xylene, diethyl ether, glycol, diethyl ether, petroleum ether, hexane, cyclohexane, pentane, methylene chloride, chloroform, carbon tetrachloride, dioxane, tetrahydrofuran (THF), dimethyl sulfoxide (DMSO), dimethylformamide, hexamethyl-phosphoric triamide, ethyl acetate, pyridine, triethylamine, picoline, mixtures thereof, or the like.

The MOFs may be synthesized at any suitable temperature. In some cases, the reaction is carried out at about room temperature (e.g., about 25° C., about 20° C., between about 20° C. and about 25° C., or the like). In some cases, however, the reaction is carried out at temperatures below or above room temperature. In some embodiments, the reaction is carried at a temperature between about 25° C. and about 200° C., about 25° C. and about 150° C., or between about 50° C. and about 200° C., or between about 50° C. and about 150° C., or between about 100° C. and about 150° C.

In some embodiments, the MOFs may be synthesized in the presence of a base (e.g., to aid in deprotonation of the ligand). Non-limiting examples of bases include NR"3 wherein each R" is the same or different and is hydrogen, optionally substituted alkyl, or optionally substituted aryl, and QOH, wherein Q is a cation (e.g., a metal cation, a semi-metal cation, $NH_4$).

In some embodiments, the MOFs may be synthesized in an inert atmosphere. For example, the reactions may be carried out in or under an inert nitrogen or argon atmosphere (e.g., using standard Schlenk techniques and/or in an inert-atmosphere glovebox).

MOFs synthesized using the methods described herein may be purified using techniques known to those of ordinary skill in the art. In some embodiments, a synthesized MOF may be washed, sometimes involving a Soxhlet extractor, boiled, and/or sonicated (e.g., to remove excess starting materials).

Definitions

For convenience, certain terms employed in the specification, examples, and appended claims are listed here.

As used herein, the term "reacting" refers to the forming of a bond between two or more components to produce a stable, isolable compound. For example, a first component and a second component may react to form one reaction product comprising the first component and the second component joined by a covalent bond. That is, the term "reacting" does not refer to the interaction of solvents, catalysts, bases, ligands, or other materials which may serve to promote the occurrence of the reaction with the component(s).

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, the term "alkyl" is given its ordinary meaning in the art and refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some cases, the alkyl group may be a lower alkyl group, i.e., an alkyl group having 1 to 10 carbon atoms (e.g., methyl, ethyl, propyl, butyl, pentyl, hexyl, heptyl, octyl, nonyl, or decyl). In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, t-butyl, cyclobutyl, hexyl, and cyclohexyl.

The term "alkylene" as used herein refers to a bivalent alkyl group. An "alkylene" group is a polymethylene group, i.e., —$(CH_2)_z$—, wherein z is a positive integer, e.g., from 1 to 20, from 1 to 10, from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described herein for a substituted aliphatic group.

Generally, the suffix "-ene" is used to describe a bivalent group. Thus, any of the terms defined herein can be modified with the suffix "-ene" to describe a bivalent version of that moiety. For example, a bivalent carbocycle is "carbocyclylene", a bivalent aryl ring is "arylene", a bivalent benzene ring is "phenylene", a bivalent heterocycle is "heterocyclylene", a bivalent heteroaryl ring is "heteroarylene", a bivalent alkyl chain is "alkylene", a bivalent alkenyl chain is "alkenylene", a bivalent alkynyl chain is "alkynylene", a bivalent heteroalkyl chain is "heteroalkylene", a bivalent heteroalkenyl chain is "heteroalkenylene", a bivalent heteroalkynyl chain is "heteroalkynylene", and so forth.

The terms "alkenyl" and "alkynyl" are given their ordinary meaning in the art and refer to unsaturated aliphatic groups analogous in length and possible substitution to the alkyls described above, but that contain at least one double or triple bond respectively.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, t-butyl, n-pentyl, sec-pentyl, isopentyl, t-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "cycloalkyl," as used herein, refers specifically to groups having three to ten, preferably three to seven carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or hetercyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl" is given its ordinary meaning in the art and refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, alkoxyalkyl, amino, thioester, poly(ethylene glycol), and alkyl-substituted amino.

The terms "heteroalkenyl" and "heteroalkynyl" are given their ordinary meaning in the art and refer to unsaturated aliphatic groups analogous in length and possible substitution to the heteroalkyls described above, but that contain at least one double or triple bond respectively.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CHF$_2$; —CH$_2$F; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "aryl" is given its ordinary meaning in the art and refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. Substituents include, but are not limited to, any of the previously mentioned substituents, i.e., the substituents recited for aliphatic moieties, or for other moieties as disclosed herein, resulting in the formation of a stable compound. In some cases, an aryl group is a stable mono- or polycyclic unsaturated moiety having preferably 3-14 carbon atoms, each of which may be substituted or unsubstituted. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups.

The terms "heteroaryl" is given its ordinary meaning in the art and refers to aryl groups comprising at least one heteroatom as a ring atom. A "heteroaryl" is a stable heterocyclic or polyheterocyclic unsaturated moiety having preferably 3-14 carbon atoms, each of which may be substituted or unsubstituted. Substituents include, but are not limited to, any of the previously mentioned substituents, i.e., the substitutes recited for aliphatic moieties, or for other moieties as disclosed herein, resulting in the formation of a stable compound. In some cases, a heteroaryl is a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl moieties, as defined herein may be attached via an alkyl or heteroalkyl moiety and thus also include -(alkyl)aryl, -(heteroalkyl)aryl, -(heteroalkyl)heteroaryl, and -(heteroalkyl) heteroaryl moieties. Thus, as used herein, the phrases "aryl or heteroaryl moieties" and "aryl, heteroaryl, -(alkyl)aryl, -(heteroalkyl)aryl, -(heteroalkyl)heteroaryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$F; —CHF$_2$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

The terms "halo" and "halogen" as used herein refer to an atom selected from the group consisting of fluorine, chlorine, bromine, and iodine.

It will be appreciated that the above groups and/or compounds, as described herein, may be optionally substituted with any number of substituents or functional moieties. That is, any of the above groups may be optionally substituted. As used herein, the term "substituted" is contemplated to include all permissible substituents of organic compounds, "permissible" being in the context of the chemical rules of valence known to those of ordinary skill in the art. In general, the term "substituted" whether preceeded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

The following examples are intended to illustrate certain embodiments of the present invention, but do not exemplify the full scope of the invention.

EXAMPLES

Example 1

The following example demonstrates the synthesis and structure of an exemplary MOF for use as a catalyst in ethylene dimerization.

Figure 2:
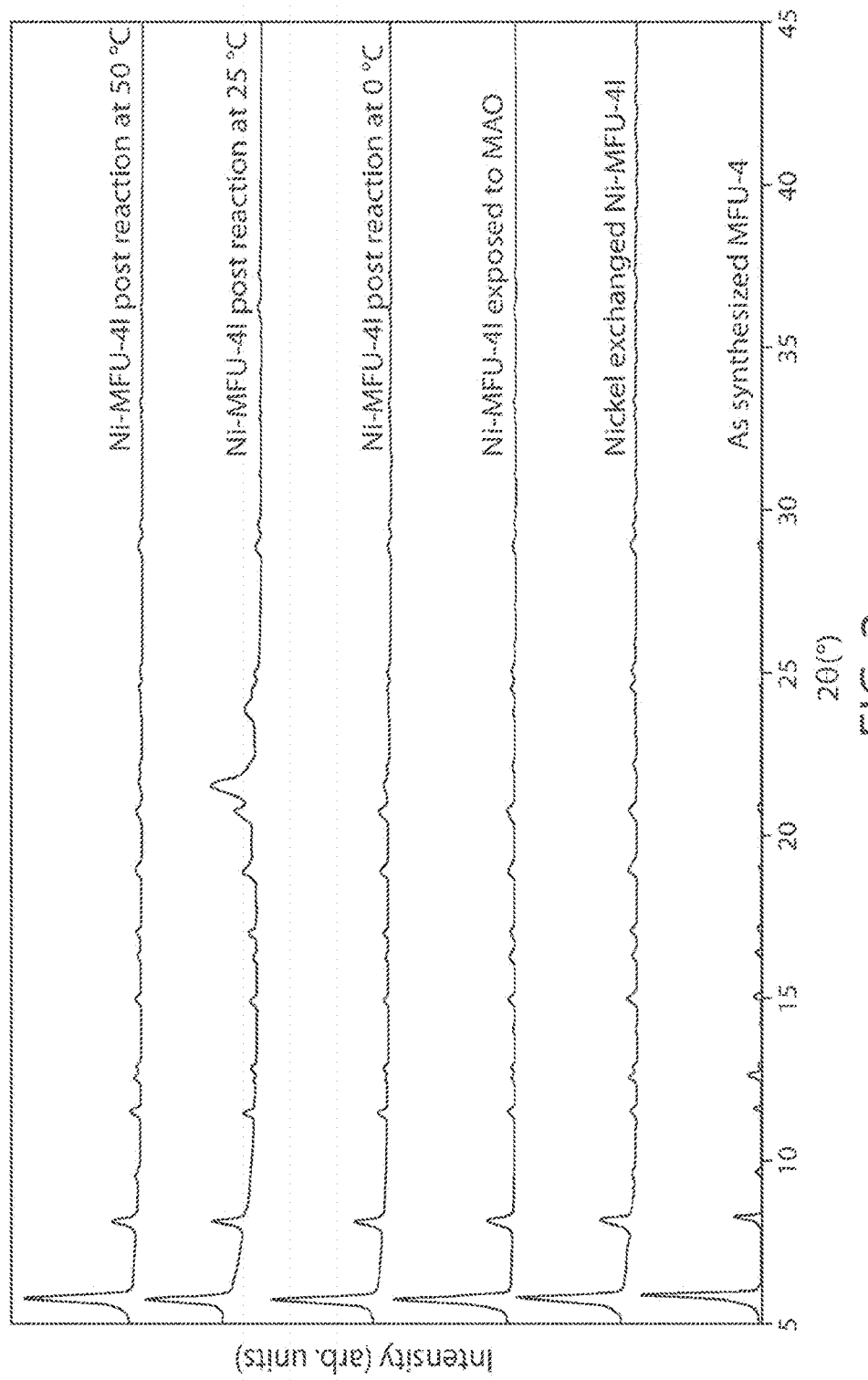
FIG. 2 shows PXRD patterns of a non-limiting MOF, after ethylene oligomerization reactions, according to some embodiments.

Four of the five $Zn^{2+}$ ions in $Zn_5Cl_4(BTDD)_3$ (MFU-4l) are coordinated to contain a central Zn atom that is octahedrally coordinated by six nitrogen atoms, and four pore-exposed tetrahedral $Zn^{2+}$ ions coordinated by three nitrogen atoms and a chloride (FIGS. 1A-1D). BTDD=bis(1H-1,2,3-triazolo[4,5-b],[4',5'-i])dibenzo[1,4]dioxin. The bond angles and lengths surrounding these $Zn^{2+}$ ions suggest that nickel-substituted MFU-4l could serve as a very proficient heterogeneous catalyst for ethylene dimerization. Soaking the parent zinc framework in a N,N-dimethylformamide (DMF) solution of $Ni(NO_3)_2 \cdot 6H_2O$ for one month produced a nickel-substituted material, $Ni_{0.46}Zn_{4.54}Cl_{2.38}(NO_3)_{1.62}(BTDD)_3$(Ni-MFU-4l), where approximately one $Zn^{2+}$ ion in every two SBUs was replaced by $Ni^{2+}$, as revealed by inductively-coupled plasma atomic emission spectroscopy (ICP-AES). To remove excess metal ions physisorbed in the pores of the framework, Ni-MFU-4l was successively soaked in fresh DMF and methanol. The structural integrity of the material was maintained during these manipulations, as evidenced by the powder X-ray diffraction (PXRD) analysis (FIG. 2). $N_2$ adsorption isotherms for activated Ni-MFU-4l revealed an uptake of 622 $cm^3$/g at 77 K and 760 torr, and a BET surface area of 2711 $m^2$/g, in line with the values reported for the parent Zn material.

Example 2

This example demonstrates the use of the MOF described in Example 1 as a catalyst in ethylene dimerization.

Figure 3:
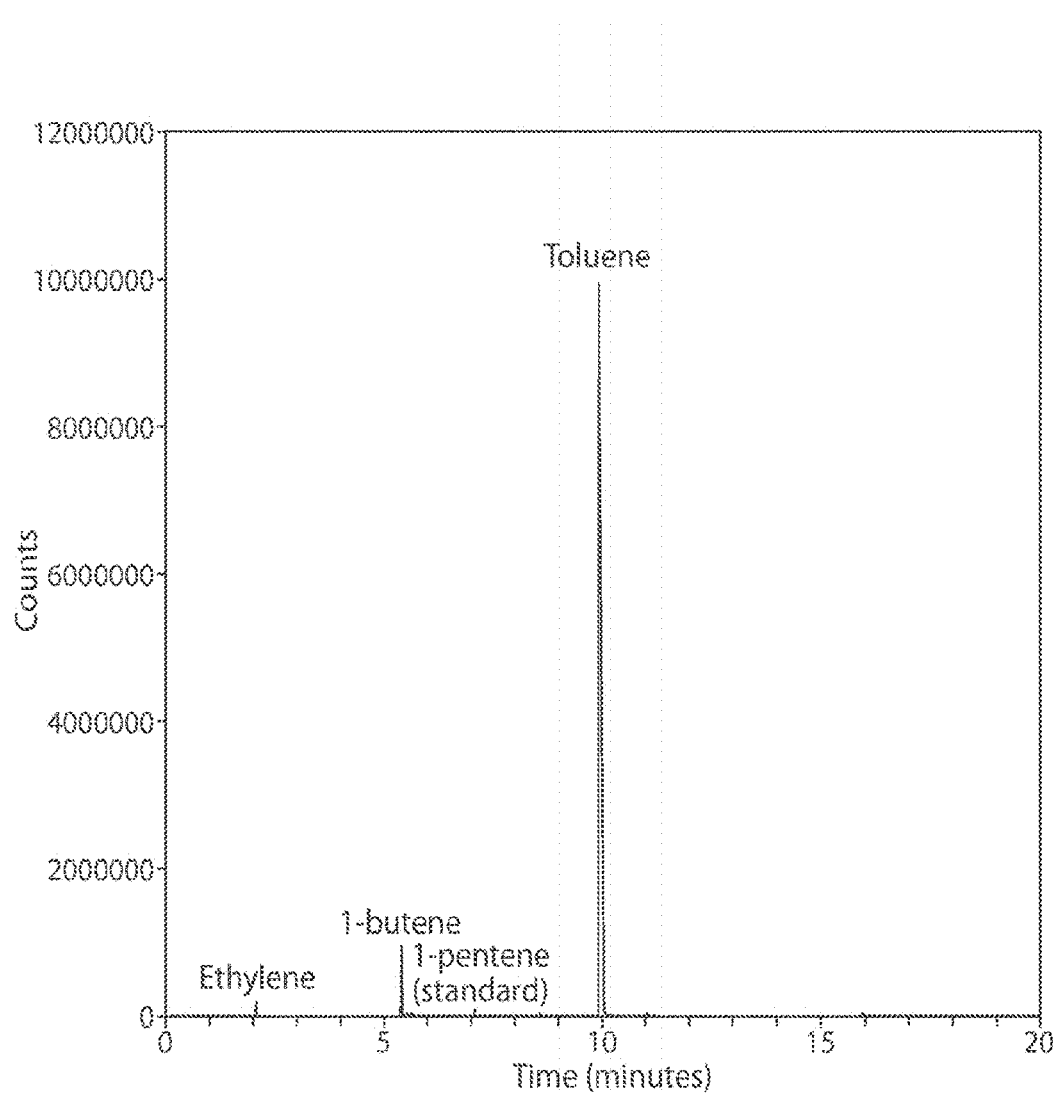
FIG. 3 and FIG. 4 show exemplary chromatograms after ethylene dimerization with a non-limiting MOF, according to some embodiments.
Figure 4:
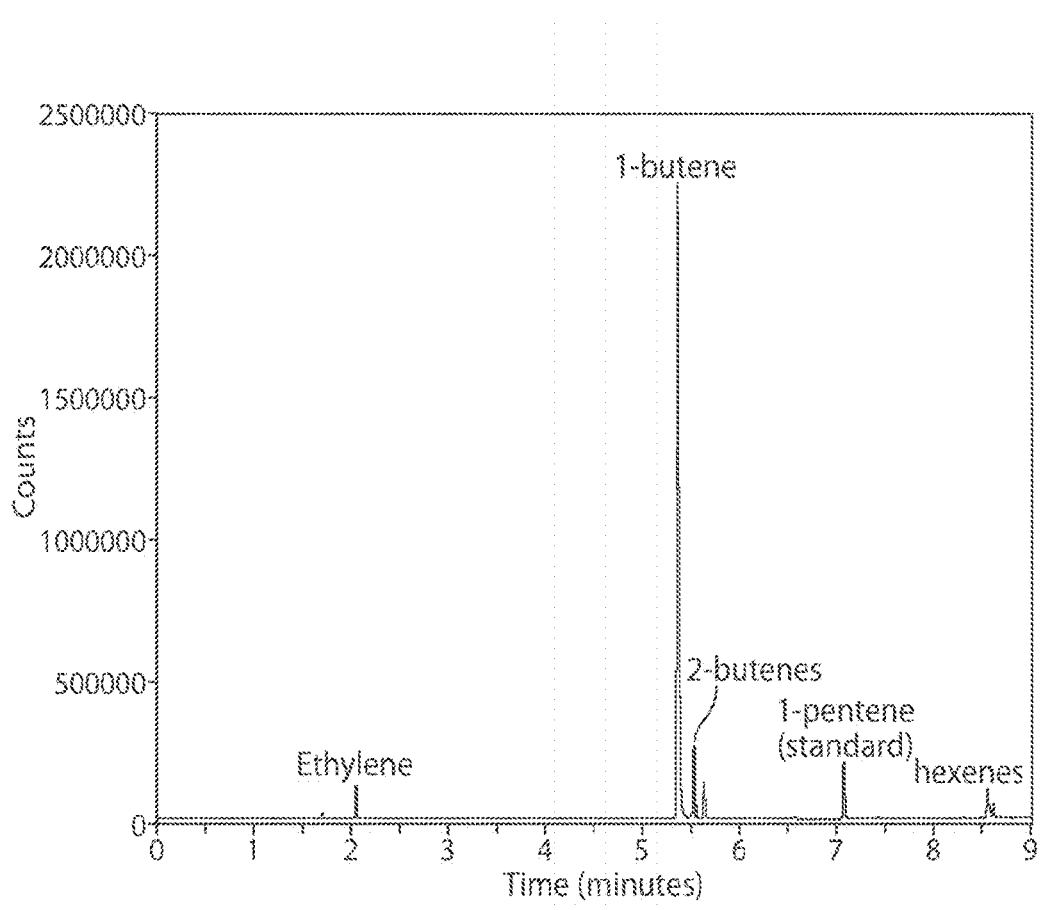
Figure 5:
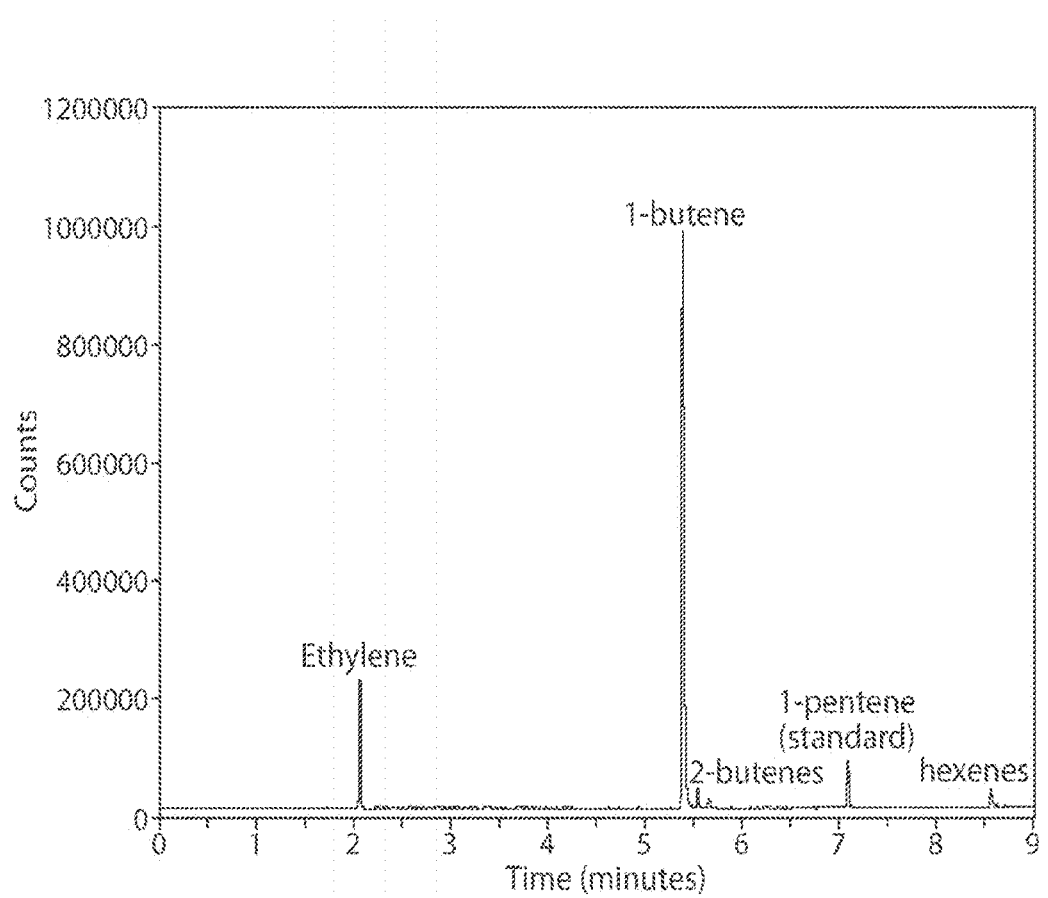
FIG. 5 shows another exemplary chromatogram after ethylene dimerization with a non-limiting MOF, according to some embodiments.

Ni-MFU-4l displays excellent activity for ethylene dimerization (see Table 1A and 1B) and compared to alternative catalysts. A typical catalytic run consisted of the addition of methylaluminoxane (MAO) to a rapidly stirred suspension of Ni-MFU-4l in toluene, with subsequent pressurization with ethylene gas. Upon completion, the reactor was rapidly cooled with a dry ice/acetone bath to condense the oligomerized products, the reaction was quenched with cooled water, and 1-pentene was added as an external standard before the organic layer was analyzed by gas chromatography (see FIG. 3, FIG. 4, and FIG. 5). After 60 minutes at 25° C., 30 bar of ethylene, and in the presence of 100 equivalents of MAO, Ni-MFU-4l showed a turnover frequency of 21,800 moles of ethylene consumed per mole of Ni per hour. The reaction products contained 94.4 wt % butenes, of which 1-butene accounted for 86.0 wt %, and 5.6 wt % hexenes. The reaction temperature had a dramatic effect on the catalytic performance of Ni-MFU-4l. For a given ethylene pressure, the dimerization activity was comparable at 0° C. and 25° C., but showed a marked drop-off when the temperature was increased to 50° C. Increasing the temperature also decreased the selectivity for 1-butene in favor of the isomerized, less desirable product 2-butene. Thus, at 50° C., 30 bar of ethylene, and 100 equivalents of MAO, the activity dropped to 1,600 $hr^{-1}$, and 1-butene represented only 83.1% of all butenes.

The reaction pressure also played a role in the catalytic performance, showing a positive correlation with the activity. At 0° C. and 100 equivalents of MAO, increasing the pressure from 15 bar to 30 bar elevated the turnover frequency from 6,300 $hr^{-1}$ to 22,600 $hr^{-1}$. The selectivity for 1-butene relative to 2-butene also generally increased with increasing pressure, with the only exception to this trend coming from the less active reactions at 50° C. This suggests that higher ethylene pressure enhanced the rate of chain transfer relative to chain isomerization, leading to the enrichment of alpha-olefins within the product distribution.

MAO additive generally improved catalytic activity in Ni-MFU-4l. When treated with an equivalent amount of $Et_2AlCl$, the turnover frequency of Ni-MFU-4l was 4,700 $hr^{-1}$, and polymeric residues were observed. The amount of MAO, and other additives, generally correlated with the observed catalytic activity. The most substantial increase was observed when the quantity of MAO was doubled from 50 to 100 equivalents.

In a first non-limiting embodiment, a turnover frequency of 27,100 moles of ethylene consumed per mole of nickel per hour was reached in the presence of 500 equivalents of MAO at 50 bar and 25° C. Under these conditions, the catalyst showed a selectivity of 96.9% for butenes, with 1-butene accounting for 92.9% of C4 products. In a second non-limiting embodiment, a turnover frequency of 41,500 moles of ethylene consumed per mole of nickel per hour was reached in the presence of 500 equivalents of MAO at 50 bar and 25° C. when the nickel loading level was decreased to 1 percent of the total metal content of the MOF. Under these conditions, the catalyst showed a selectivity of 97.4% for butenes, with 1-butene accounting for 94.5% of C4 products. The selectivity for 1-butene increased when catalysis was run with 100 equivalents of MAO at 50 bar and 0° C. These conditions lead to a turnover frequency of 22,600 moles of ethylene consumed per mole of nickel per hour and an optimized selectivity of 98.4% for butenes, with 1-butene making up 97.8% of the C4 fraction. Indeed, the optimized overall selectivity for 1-butene was thus 96.2%.

Under these conditions, Ni-MFU-4l produced C6 olefins as the sole byproducts. In an industrial setting these oligomers will not typically foul the reactor, can readily be separated using technology currently employed in the Alphabutol process, and are valuable themselves as copolymerization monomers. The high activity suggests that all of the nickel sites are active, not just those exposed on the surface.

Without wishing to be bound by theory, shape selectivity induced by the pores of the MOF may explain the preference for butenes relative to hexenes, although this does not account for the higher 1-butene selectivity observed with the heterogeneous catalyst. An alternative explanation is that the less sterically encumbered active site in the MOF enhances the rate of chain transfer relative to chain propagation or chain isomerization. The Ni environment within Ni-MFU-4l provides an ideal balance between active site accessibility and pore-induced shape selectivity, which lead to unprecedented selectivity for 1-butene.

Figure 6:
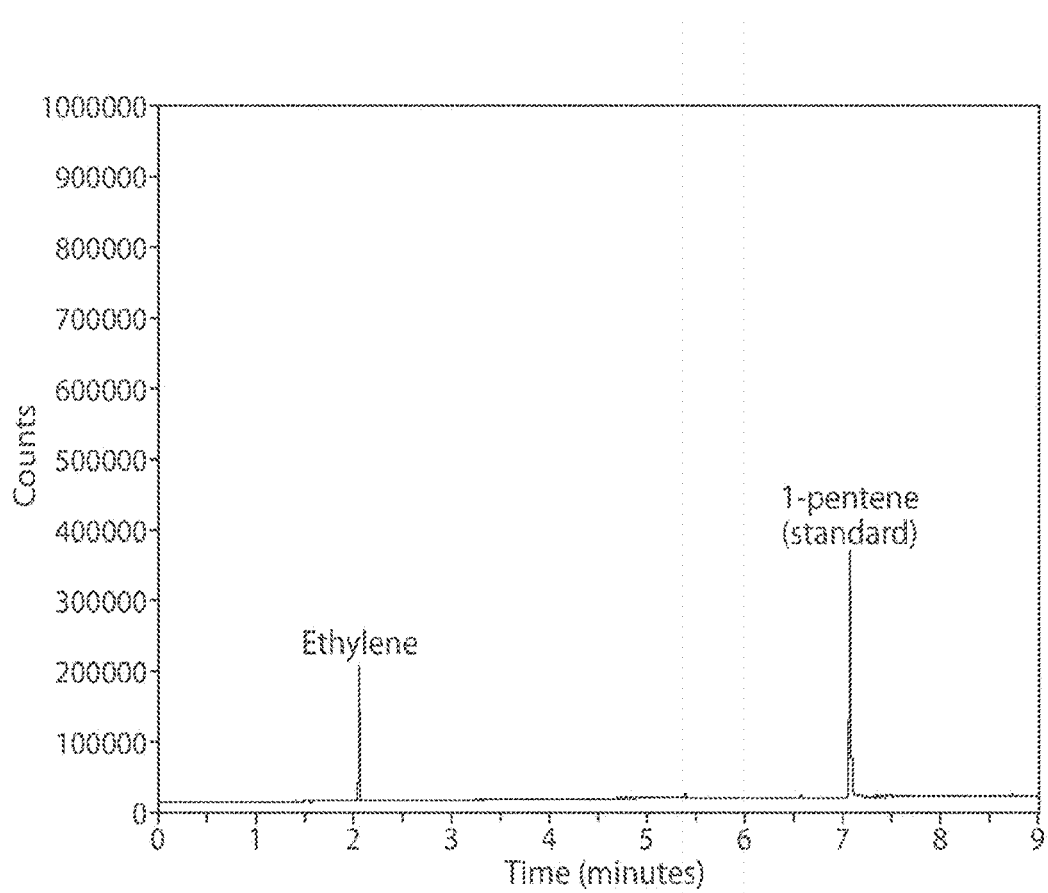
FIG. 6 shows an exemplary chromatogram for ethylene dimerization with a comparative MOF, according to some embodiments.
Figure 7:
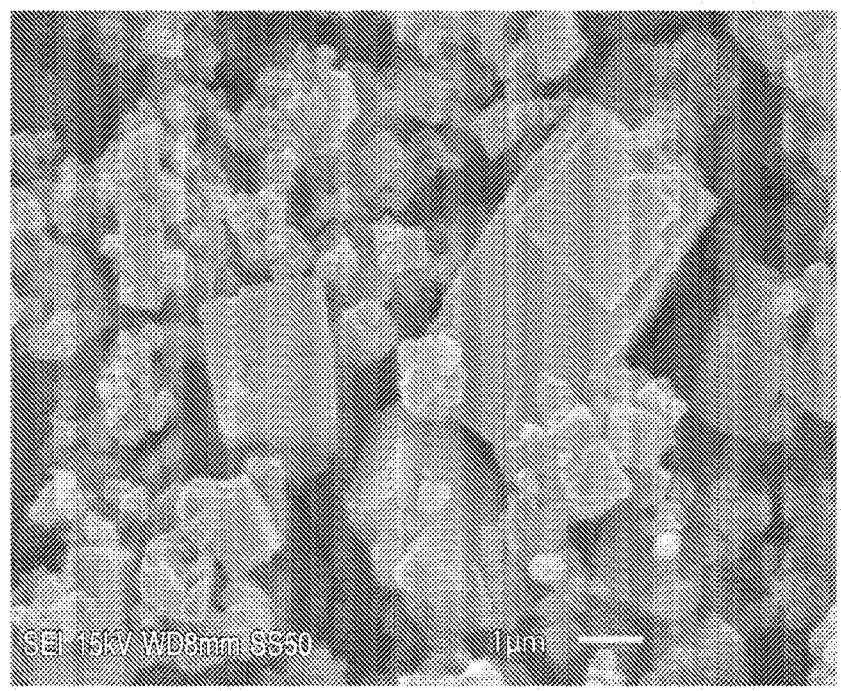
FIG. 7 shows a scanning electron microscope image of non-limiting MOF particles, according to some embodiments.

To determine whether the nickel sites in Ni-MFU-4l were responsible for the catalytic activity, standard dimerization reactions with unsubstituted, all-zinc MFU-4l were conducted. No product formation was observed, indicating that the nickel sites are necessary for dimerization activity. Furthermore, leaching tests showed that the reaction no longer proceeded if the MOF was filtered and removed from the reactor, confirming that the catalytic activity was not attributable to trace homogeneous decomposition products of the MOF (FIG. 6). Finally, PXRD analysis ensured that Ni-MFU-4l remained crystalline after catalysis (FIG. 2).

Example 3

The following example demonstrates the lifetime of the MOF catalyst described in Example 1.

One of the major attractions in heterogenizing homogeneous catalysts stems from the possibility of extending the catalyst lifetime by eliminating bimolecular decomposition pathways. To study the lifetime of Ni-MFU-4l and the potential for catalyst recycling, a two-reactor system that allowed distillation of the reaction products without exposing the Ni-MFU-4l/MAO slurry to the atmosphere was constructed. This experimental setup allowed the removal of products by distillation and repressurization of the reactor for evaluating the catalyst in consecutive runs. The reactor was thus cycled continuously over 72 hours (8 cycles), with only a minor decrease in catalyst activity (See Table 2). Over the course of these 8 cycles, over 92,000 moles of ethylene were dimerized per mole of nickel, highlighting the robustness of Ni-MFU-4l for catalytic ethylene dimerization.

TABLE 1A

Results of ethylene oligomerization with Ni-MFU-4l.

| | | | | | Selectivity (wt %) | | |
|---|---|---|---|---|---|---|---|
| Entry | Pressure (bar) | T (° C.) | MAO equivs | TOF $(hr^{-1})^a$ | C4 | C6 | α-C4 |
| 1 | 50 | 25° C. | 500 | 27000 | 96.53 | 3.47 | 92.31 |
| 2 | 50 | 25° C. | 250 | 26700 | 97.36 | 2.64 | 93.70 |
| 3 | 50 | 25° C. | 100 | 23300 | 97.14 | 2.86 | 93.59 |
| 4 | 50 | 25° C. | 50 | 5900 | 95.77 | 4.23 | 84.72 |
| 5 | 50 | 0° C. | 100 | 22600 | 98.35 | 1.65 | 97.81 |
| 6 | 50 | 25° C. | 100 | 23300 | 97.14 | 2.86 | 93.59 |
| 7 | 50 | 50° C. | 100 | 1700 | 87.51 | 12.49 | 80.52 |
| 8 | 30 | 0° C. | 100 | 21600 | 97.43 | 2.57 | 95.50 |
| 9 | 30 | 25° C. | 100 | 21800 | 94.41 | 5.59 | 85.98 |
| 10 | 30 | 50° C. | 100 | 1600 | 89.34 | 10.66 | 83.14 |
| 11 | 15 | 0° C. | 100 | 6300 | 94.17 | 5.83 | 93.54 |
| 12 | 15 | 25° C. | 100 | 11100 | 94.75 | 5.25 | 80.73 |
| 13 | 15 | 50° C. | 100 | 600 | 85.19 | 14.81 | 79.30 |

$^a$Moles of ethylene converted per mole of nickel per hour, determined by GC analysis.

TABLE 1B

Ethylene dimerization with Ni-MFU-4l.

| | | | | | Selectivity (wt %) | | | |
|---|---|---|---|---|---|---|---|---|
| Entry | Pressure (bar) | T (° C.) | MAO equivs | TOF $(h^{-1})^e$ | $C_4^f$ | $C_6^g$ | α-$C_4^h$ | Overall 1-butene$^i$ |
| 1$^a$ | 50 | 25 | 500 | 27000 | 96.5 | 3.5 | 92.3 | 89.1 |
| 2$^a$ | 50 | 25 | 250 | 26700 | 97.4 | 2.6 | 93.7 | 91.3 |
| 3$^a$ | 50 | 25 | 100 | 21000 | 97.2 | 2.8 | 94.6 | 92.0 |
| 4$^a$ | 50 | 25 | 50 | 5900 | 95.8 | 4.2 | 84.7 | 81.1 |
| 5$^a$ | 50 | 0 | 100 | 22600 | 98.4 | 1.6 | 97.8 | 96.2 |
| 6$^a$ | 50 | 25 | 100 | 21000 | 97.2 | 2.8 | 94.6 | 92.0 |
| 7$^a$ | 50 | 50 | 100 | 1700 | 87.5 | 12.5 | 80.5 | 70.4 |
| 8$^a$ | 30 | 0 | 100 | 21600 | 97.4 | 2.6 | 95.5 | 93.0 |
| 9$^a$ | 30 | 25 | 100 | 21000 | 95.2 | 4.8 | 86.9 | 82.7 |
| 10$^a$ | 30 | 50 | 100 | 1600 | 89.3 | 10.7 | 83.1 | 74.2 |
| 11$^a$ | 15 | 0 | 100 | 6300 | 94.2 | 5.8 | 93.5 | 88.1 |
| 12$^a$ | 15 | 25 | 100 | 11100 | 94.8 | 5.2 | 80.7 | 76.5 |
| 13$^a$ | 15 | 50 | 100 | 600 | 85.2 | 14.8 | 79.3 | 67.6 |
| 14$^a$ | 5 | 25 | 100 | 3600 | 92.9 | 7.1 | 72.8 | 67.6 |
| 15$^a$ | 10 | 25 | 100 | 7000 | 94.4 | 5.6 | 80.8 | 76.3 |
| 16$^a$ | 15 | 25 | 100 | 11100 | 94.8 | 5.2 | 80.7 | 76.5 |
| 17$^a$ | 20 | 25 | 100 | 16400 | 94.9 | 5.1 | 81.9 | 77.7 |
| 18$^a$ | 25 | 25 | 100 | 19800 | 95.7 | 4.3 | 86.8 | 83.1 |
| 19$^a$ | 30 | 25 | 100 | 21000 | 95.2 | 4.8 | 86.9 | 82.7 |
| 20$^a$ | 40 | 25 | 100 | 20000 | 96.6 | 3.4 | 94.3 | 91.1 |
| 21$^a$ | 50 | 25 | 100 | 21000 | 97.2 | 2.8 | 94.6 | 92.0 |
| 22$^b$ | 50 | 25 | 500 | 9100 | 97.3 | 2.7 | 93.0 | 90.5 |
| 23$^a$ | 50 | 25 | 500 | 27000 | 96.5 | 3.5 | 92.3 | 89.1 |
| 24$^c$ | 50 | 25 | 500 | 39600 | 97.3 | 2.7 | 94.7 | 92.1 |
| 25$^d$ | 50 | 25 | 500 | 41500 | 97.4 | 2.6 | 94.5 | 92.0 |

Results of ethylene dimerization with Ni-MFU-4l, as determined by GC analysis.
$^a$Catalyst is Ni(10%)-MFU-4l
$^b$Catalyst is Ni(30%)-MFU-4l
$^c$Catalyst is Ni(3%)-MFU-4l
$^d$Catalyst is Ni(1%)-MFU-4l
$^e$Moles of ethylene converted per mole of nickel per hour, determined by GC analysis.
$^f$Percent oligomeric products that are C$_4$ olefins.
$^g$Percent oligomeric products that are C$_6$ olefins.
$^h$Percent 1-butene relative to all C$_4$ products.
$^i$The overall selectivity for 1-butene among all products.

TABLE 2

Results of the lifetime experiments with Ni-MFU-4l where the products are distilled off into a second reactor.

| | | Selectivity (wt %) | | | |
|---|---|---|---|---|---|
| Cycle | Turnovers$^a$ | C4 | C6 | C8 | α-C4 |
| 1 | 13600 | 99.35 | 0.65 | — | 93.88 |
| 2 | 12100 | 99.18 | 0.82 | — | 88.78 |
| 3 | 10200 | 99.02 | 0.98 | — | 84.73 |
| 4 | 11000 | 98.65 | 1.35 | — | 82.82 |
| 5 | 12000 | 98.22 | 1.78 | — | 84.00 |
| 6 | 12000 | 98.15 | 1.85 | — | 85.54 |
| 7 | 11000 | 98.29 | 1.71 | — | 85.35 |
| 8 | 11200 | 98.86 | 1.14 | — | 84.74 |

$^a$Turnovers defined as the moles of ethylene converted per nickel site. Each cycle lasts for 1 hour.

Example 4

The following example demonstrates the synthesis and structure of an exemplary MOF for use as a catalyst in ethylene dimerization.

Figure 8A:
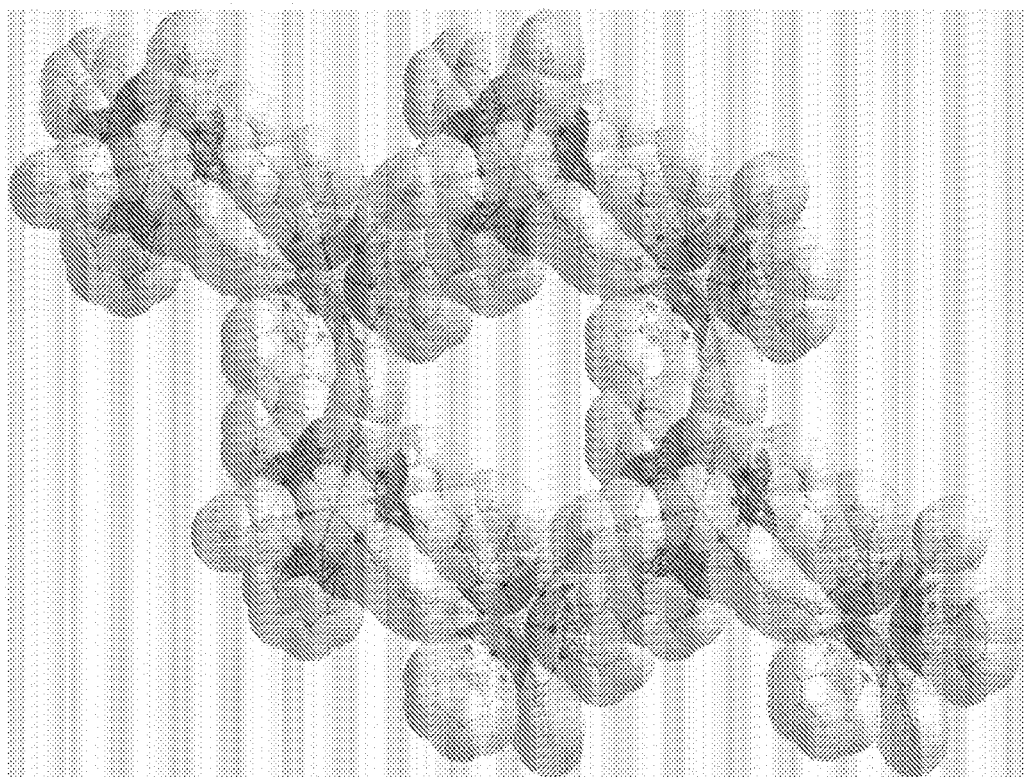
FIG. 8A-FIG. 8C show simulated structure of a non-limiting example of an MOF.
Figure 8B:
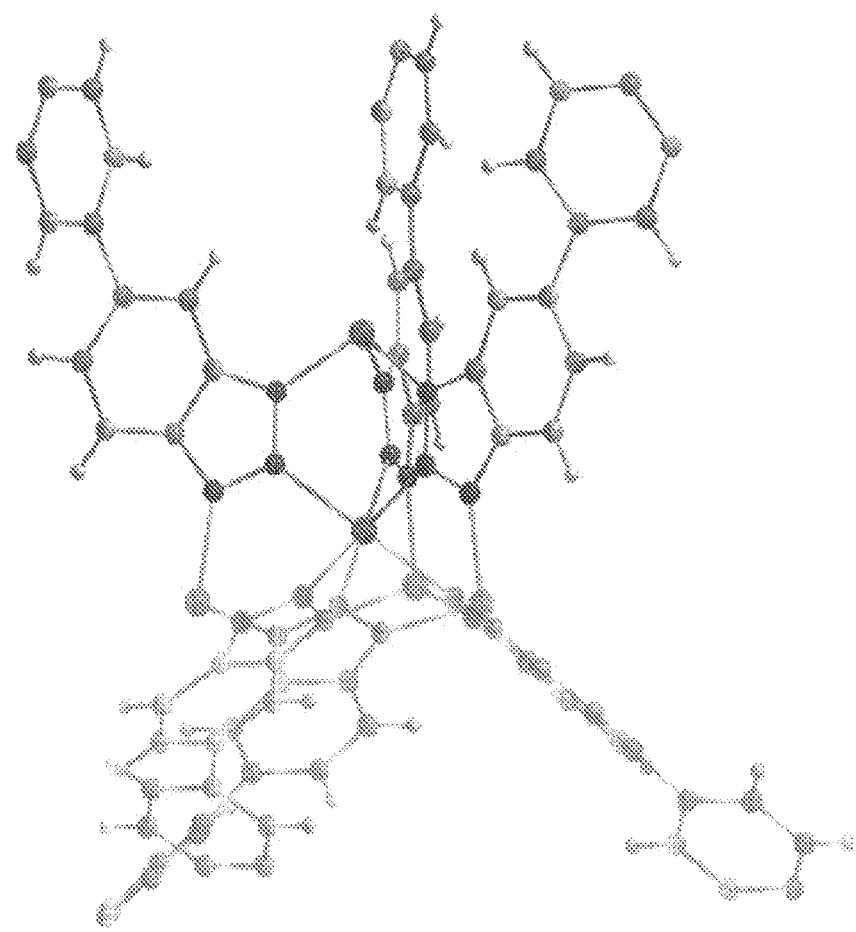
Figure 8C:
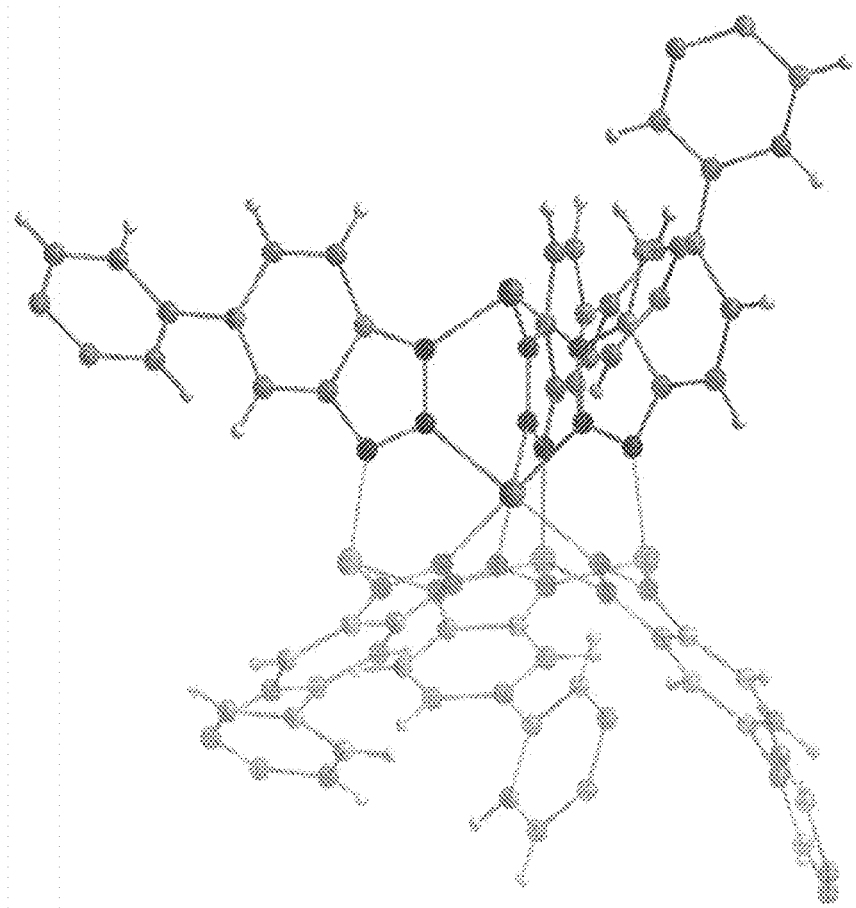

Four of the five $Zn^{2+}$ ions in $Zn_5Cl_4(bibta)_3$ (CFA-1) are coordinated to contain a central Zn atom that is octahedrally coordinated by six nitrogen atoms, and four pore-exposed tetrahedral $Zn^{2+}$ ions coordinated by three nitrogen atoms and a chloride (FIG. 8A-FIG. 8C). bibta=1H,1'H-5,5'-bibenzo[d]triazole. The bond angles and lengths surrounding these $Zn^{2+}$ ions suggest that nickel-substituted CFA-1 may be a very proficient heterogeneous catalyst for ethylene dimerization. Soaking the parent zinc framework in a N,N-dimethylformamide (DMF) solution of $Ni(NO_3)_2 \cdot 6H_2O$ for one month produced a nickel-substituted material, $Ni_{0.34}Zn_{4.66}Cl_4(bibta)_3$ (Ni-CFA-1), where approximately one $Zn^{2+}$ ion in every three SBUs was replaced by $Ni^{2+}$, as revealed by inductively-coupled plasma atomic emission spectroscopy (ICP-AES). To remove excess metal ions physisorbed in the pores of the framework, Ni-CFA-1 was successively soaked in fresh DMF and methanol. The structural integrity of the material was maintained during these manipulations, as evidenced by the powder X-ray diffraction.

Example 5

This example demonstrates the use of the MOF described in Example 4 as a catalyst in ethylene dimerization.

Ni-CFA-1 displays excellent activity for ethylene dimerization compared to alternative catalysts. A typical catalytic run involved the addition of modified methylaluminoxane (MMAO-12) to a rapidly stirred suspension of Ni-CFA-1 in toluene, with subsequent pressurization with ethylene gas. Upon completion, the reactor was rapidly cooled with a dry ice/acetone bath to condense the oligomerized products, the reaction was quenched with cooled water, and 1-pentene was added as an external standard before the organic layer was analyzed by gas chromatography. At 25° C. and 1000 equivalents of MMAO-12 the turnover frequency is 36,400 with a selectivity of 96% for butenes and a selectivity of 90% for 1-butene relative to all $C_4$ products. The selectivity for 1-butene relative to 2-butene also generally increased with increasing pressure. This suggests that higher ethylene pressure enhanced the rate of chain transfer relative to chain isomerization, leading to the enrichment of alpha-olefins within the product distribution.

Example 6

This example outlines the methods used in Examples 1-5.

Powder X-ray diffraction (PXRD) patterns were recorded on a Bruker Advance II diffractometer equipped with θ/2θ Bragg-Brentano geometry and Ni-filtered Cu-Kα radiation (Kα1=1.5406 Å). The tube voltage and current were 40 kV and 40 mA, respectively.

A Micromeritics ASAP 2020 Surface Area and Porosity Analyzer was used to measure nitrogen adsorption isotherms. An oven-dried sample tube equipped with a S3 TranSeal™ (Micrometrics) was evacuated and tared. The sample was transferred to the sample tube, heated to 200° C. for 12 h, and held at that temperature until the outgas rate was less than 2 mtorr/minute. The evacuated sample tube was weighed again and the sample mass was determined by subtracting the mass of the previously tared tube. An $N_2$ isotherm was measured using liquid nitrogen baths (77 K). UHP grade (99.999% purity) $N_2$ and He, oil-free valves and gas regulators were used for all free space corrections and measurements.

The ethylene dimerization reaction mixtures were analyzed with an Agilent 7890B gas chromatograph (30 meter PoraBOND Q PT capillary column) equipped with a 5977A mass spectrometer and a flame ionization detector.

Synthesis of H2BTDD, Linker for MFU-4l.

A solution of $NaNO_2$ (2.86 g, 41.4 mmol) and water (10 mL) was added over ten minutes into a stirring, ice-cooled suspension of dibenzo[1,4]dioxine-2,3,7,8-tetramine tetrakis hydrochloride (7.35 g, 18.8 mmol), acetic acid (70 mL), and water (10 mL). After the transfer was complete, the resulting suspension was allowed to stir an additional 30 minutes. The title compound was obtained by filtration, rinsing with water (50 mL) and methanol (50 mL), as a tan powder (4.31 g, 16.2 mmol, 86% yield). $^1$H NMR (500 MHz, trifluoroacetic acid-D1) δ 7.65 (4H). $^{13}$C NMR (125 MHz, trifluoroacetic acid-D1) δ 145.25, 131.72, 100.40.

Synthesis of $Zn_5Cl_4(BTDD)_3$.

H2BTDD (1.00 g, 3.76 mmol) was heated with stifling in DMF (1.0 L) at 140° C. until a homogeneous solution was obtained. The solution was then cooled down to room temperature before the addition of $ZnCl_2$. The mixture was heated to 140° C. with stirring overnight. The resulting powder was obtained by filtration and rinsed with DMF. The powder was soaked in DMF for 12 hours before isolation via centrifugation. This soaking process was repeated four times with DMF, and then two additional times with methanol. The sample was then filtered, rinsed with dichloromethane, and then dried under high vacuum overnight at 180° C.

Synthesis of $Ni_{0.46}Zn_{4.54}Cl_{2.38}(NO_3)_{1.62}(BTDD)_3$.

$Ni(NO_3)_2 \cdot 6H_2O$ (5.5 g, 19 mmol) was dissolved in 100 mL of DMF. MFU-4l was suspended in an additional 50 mL of DMF and added to the $Ni(NO_3)_2 \cdot 6H_2O$ solution. The resulting suspension was allowed to sit at room temperature for one month. The solution was decanted, and the remaining powder was soaked in 100 mL fresh DMF. This process was repeated once daily for three days. The powder was subsequently suspended in 100 mL of fresh methanol. The methanol was replaced once daily for three days. The resulting powder was collected via gravity filtration and was transferred into activation glassware. The material was activated at 150° C. under high vacuum.

General Procedure for Ethylene Oligomerization.

In the typical catalytic run, a magnetic stir bar and 5 mg of thermally desolvated Ni-MFU-4l were introduced into a 50 mL stainless steel Parr reactor in a nitrogen filled glovebox. 5 mL of toluene were added to the reactor, followed by the addition of the specified number of equivalents of methylaluminoxane (10% w/w in toluene, Aldrich). The reactor was fully sealed, transferred out of the glovebox, and brought to the reaction temperature specified with a temperature controller and internal temperature probe. Thirty minutes after the addition of methylaluminxoane, the reactor was pressurized with ethylene through a dip tube and magnetic stirring was turned on. After one hour, the reactor was rapidly cooled in a dry ice/acetone bath. When the internal temperature reaches −20° C., the reactor was slowly vented to atmospheric pressure. The reactor was opened and the reaction solution was treated with precooled deionized water. 1-pentene was added to the solution to serve as an external standard before the organic layer was filtered through a precooled 0.2 μm syringe filter. A small sample of the organic layer was quickly analyzed via gas chromatography. Control experiments with the unsubstituted MFU-4l or with alternative aluminum activators were carried out in the same manner as described above.

Leaching Experiment with Ni-MFU-4l.

To verify that leached nickel species were not responsible for the observed catalytic activity, a magnetic stir bar and 5 mg of thermally desolvated Ni-MFU-4l were introduced into a 50 mL stainless steel Parr reactor in a nitrogen filled glovebox. 5 mL of toluene was added to the reactor, followed by the addition of 100 equivalents of methylaluminoxane (10% w/w in toluene, Aldrich). The reactor was fully sealed, transferred out of the glovebox, and brought to the reaction temperature specified with a temperature controller and internal temperature probe. Thirty minutes after the addition of methylaluminxoane, magnetic stirring was turned on and the reactor was pressurized with ethylene through a dip tube. After one hour, the reactor was transferred into a nitrogen glove bag and slowly vented to atmospheric pressure. The reactor was opened and the reaction solution was sparged with dry nitrogen for 15 minutes to remove any residual butenes in solution. The solution was subsequently filtered through three 0.2 μm syringe filters and transferred into a new 50 mL stainless steel Parr reactor. This new reactor was fully closed, transferred out of the glove bag, and pressurized with ethylene through a dip tube. Internal stirring was maintained throughout the reaction, and after one hour the reactor was rapidly cooled to −20° C. with a dry ice/acetone bath. Once the internal temperature reached −20° C. the reactor was slowly vented to atmospheric pressure. The reactor was opened and the reaction solution was treated with precooled deionized water. 1-pentene was added to the solution to serve as an external standard before the organic layer was filtered through a precooled 0.2 μm syringe filter. A small sample of the organic layer was quickly analyzed via gas chromatography.

Lifetime Experiment with Ni-MFU-4l.

A two-reactor system that allowed the distillation the reaction product without exposing the Ni-MFU-4l/MAO slurry to air was constructed in order to study the lifetime of Ni-MFU-4l and the potential for catalyst recycling. As with typical oligomerization experiments, a magnetic stir bar and 5 mg of thermally desolvated Ni-MFU-4l were introduced into a 25 mL stainless steel Parr reactor, referred to as reactor 1, in a nitrogen filled glovebox. 5 mL of toluene was added to the reactor, followed by the addition of 100 equivalents of methylaluminoxane (10% w/w in toluene, Aldrich). The reactor was fully sealed, transferred out of the glovebox, and the temperature of the reactor was monitored with an internal temperature probe. A 50 mL stainless steel Parr reactor, referred to as reactor 2, was connected to reactor 1 with three feet of ⅛" copper tubing, although the valve connecting reactor 1 to reactor 2 was left closed. Reactor 2 was evacuated to remove ambient water and oxygen inside the vessel. After evacuation, reactor 2 was cooled below −20° C. with a dry ice/acetone bath, as monitored with an internal temperature probe. Thirty minutes after the addition of methylaluminxoane to Ni-MFU-4l, reactor 1 was pressurized to 50 bar with ethylene through a dip tube and magnetic stirring was turned on. After one hour, reactor 1 was placed in a lukewarm water bath and the connection between reactor 1 and reactor 2 was opened, allowing the product butenes to condense in the second reactor. After 30 minutes to allow the system to equilibrate, the connection between reactor 1 and reactor 2 was closed. Reactor 2 was opened, and 10 mL of precooled toluene and 0.1 mL of 1-pentene were added to the vessel. This organic mixture was analyzed via gas chromatography. Reactor 1 was repressurized with ethylene and allowed to react for one hour, while reactor 2 was cleaned and evacuated. This process was continued for 10 cycles before reactor 1 was opened and the organic products were analyzed via GC/MS.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for forming butene from ethylene, the method comprising:
exposing ethylene to a metal organic framework (MOF) catalyst to produce butene,
wherein the MOF catalyst comprises a plurality of metal ions, each metal ion coordinated with at least one ligand, and at least one metal ion being $Ni^{2+}$, and
wherein the at least one ligand comprises at least two N-heterocyclic aromatic groups arranged about an organic core, wherein the N-heterocyclic aromatic groups are selected from the group consisting of imidazolate, triazolate, and tetrazolate.

2. The method of claim 1, wherein butene is formed with a selectivity of at least about 75% and at a turnover frequency of at least about 12,500 per hour.

3. The method as in claim 1, wherein an additive is present during the exposing step.

4. The method as in claim 3, wherein the additive is selected from the group consisting of an aluminoxane, methylaluminoxane, ethylaluminum dichloride, diethylaluminum chloride, triethylaluminum, an alkyl magnesium halide an alkyllithium, and trimethylaluminum.

5. The method as in claim 3, wherein the additive is methylaluminoxane.

6. The method as in claim 1, wherein the MOF catalyst further comprises at least one metal ion selected from the group consisting of $Ti^{3+}$, $Cr^{2+}$, $Cr^{3+}$, $Mn^{2+}$, $Fe^{2+}$, $Co^{2+}$, $Cu^{2+}$, and $Zn^{2+}$.

7. The method as in claim 6, wherein at least one metal ion is $Zn^{2+}$.

8. The method as in claim 1, wherein the N-heterocyclic aromatic group is triazolate.

9. The method as in claim 1, wherein butene is formed with a selectivity of at least about 80%.

10. The method as in claim 1, wherein 1-butene is formed with a selectivity of at least about 80%.

11. The method as in claim 1, wherein butene is formed with a selectivity of at least about 80%.

12. The method as in claim 1, wherein 1-butene is formed with a selectivity of at least about 80% at a turnover frequency of at least about 12,500 per hour per active metal center.

13. The method as in claim 1, wherein the MOF comprises at least two ligands comprising triazolate.

14. The method as in claim 1, wherein the at least one ligand comprising the N-heterocyclic aromatic group has a structure as in Formula (I):

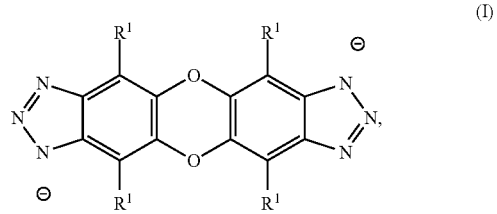

wherein each $R^1$ is the same or different and is selected from the group consisting of hydrogen, -alkyl, $-NO_2$, $-R'$, $-F$, $-Cl$, $-Br$, $-I$, $-CN$, $-NC$, $-SO_3R'$, $-SO_3H$, $-OR'$, $-OH$, $-SR'$, $-SH$, $-PO_3R'$, $-PO_3H$, $-CF_3$, $-NR'_2$, $-NHR'$, and $-NH_2$, and each R' is the same or different and is optionally substituted alkyl or optionally substituted aryl.

15. The method as in claim 14, wherein each $R^1$ is hydrogen.

16. The method as in claim 1, wherein the at least one ligand comprising the N-heterocyclic aromatic group comprises the structure:

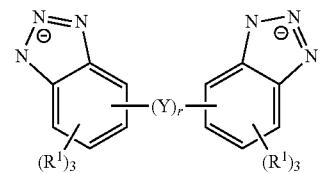

wherein each $R^1$ is the same or different and is selected from the group consisting of hydrogen, -alkyl, $-NO_2$, $-R'$, $-F$, $-Cl$, $-Br$, $-I$, $-CN$, $-NC$, $-SO_3R'$, $-SO_3H$, $-OR'$, $-OH$, $-SR'$, $-SH$, $-PO_3R'$, $-PO_3H$, $-CF_3$, $-NR'_2$, $-NHR'$, and $-NH_2$, wherein each R' is the same or different and is optionally substituted alkyl or optionally substituted aryl, wherein each Y is independently alkylene, heteroalkylene, arylene, heteroarylene, $-O-$, $-C(=O)$, $-S-$, and wherein r is 0, 1, 2, or 3.

17. The method as in claim 16, wherein the ligand has the structure:

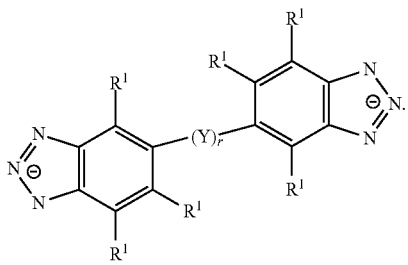

18. The method as in claim 16, wherein each $R^1$ is H.

19. The method as in claim 16, wherein r is 0.

20. The method as in claim 1, wherein butene is formed with a selectivity of at least about 90%.

21. The method as in claim 1, wherein butene is formed with a selectivity of at least about 98%.

22. The method as in claim 1, wherein butene is formed with a selectivity of about 100%.

23. The method as in claim 1, wherein butene is formed with a selectivity of at least about 80% at a turnover frequency of at least about 17,500 per hour per active metal center.

24. The method as in claim 1, wherein butene is formed with a selectivity of at least about 80% at a turnover frequency of at least about 25,000 per hour per active metal center.

25. The method as in claim 1, wherein butene is formed with a selectivity of at least about 80% at a turnover frequency of at least about 41,500 per hour per active metal center.

26. A method for forming butene from ethylene, the method comprising:
exposing ethylene to a metal organic framework (MOF) catalyst to produce butene, wherein the MOF comprises a plurality of metal ions, each metal ion coordinated with at least one ligand, and at least one metal ion being $Ni^{2+}$, and wherein butene is formed with a selectivity of at least about 95% and at a turnover frequency of at least about 20,000 per hour.

27. The method as in claim 26, wherein each ligand comprises at least two N-heterocyclic aromatic groups arranged about an organic core, wherein the N-heterocyclic aromatic groups are selected from the group consisting of pyrazolate, pyridinate, imidazolate, triazolate, and tetrazolate.

* * * * *